(12) United States Patent
Osorio

(10) Patent No.: US 10,493,020 B2
(45) Date of Patent: *Dec. 3, 2019

(54) METHOD OF IMPROVING THE APPEARANCE OF PERIORBITAL DYSCHROMIA

(71) Applicant: The Procter & Gamble Company, Cincinnati, OH (US)

(72) Inventor: Karen Marie Osorio, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 368 days.

This patent is subject to a terminal disclaimer.

(21) Appl. No.: 15/099,120

(22) Filed: Apr. 14, 2016

(65) Prior Publication Data

US 2017/0296461 A1 Oct. 19, 2017

(51) Int. Cl.

| A61K 8/97 | (2017.01) |
|---|---|
| A61K 8/06 | (2006.01) |
| A61K 8/37 | (2006.01) |
| A61K 8/42 | (2006.01) |
| A61K 8/49 | (2006.01) |
| A61K 8/60 | (2006.01) |
| A61Q 19/02 | (2006.01) |
| A61Q 19/08 | (2006.01) |
| A61Q 19/00 | (2006.01) |
| A61K 36/42 | (2006.01) |
| A61K 8/9789 | (2017.01) |
| A61K 36/21 | (2006.01) |
| A61K 36/48 | (2006.01) |

(52) U.S. Cl.
CPC .............. *A61K 8/97* (2013.01); *A61K 8/062* (2013.01); *A61K 8/37* (2013.01); *A61K 8/42* (2013.01); *A61K 8/498* (2013.01); *A61K 8/602* (2013.01); *A61K 8/9789* (2017.08); *A61K 36/21* (2013.01); *A61K 36/42* (2013.01); *A61K 36/48* (2013.01); *A61Q 19/005* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| 4,981,845 A * | 1/1991 | Pereira ............... A61K 8/06 514/558 |
|---|---|---|
| 6,641,848 B1 * | 11/2003 | Bonte ............... A61K 8/345 424/401 |
| 6,974,799 B2 | 12/2005 | Lintner |
| 7,176,172 B2 | 2/2007 | Harding |
| 7,235,249 B2 | 6/2007 | Bissett |
| 7,427,690 B2 | 9/2008 | Gupta |
| 7,476,221 B2 | 1/2009 | Sun |
| 7,476,222 B2 | 1/2009 | Sun |
| 7,477,939 B2 | 1/2009 | Sun |
| 7,477,940 B2 | 1/2009 | Sun |
| 7,477,941 B2 | 1/2009 | Sun |
| 7,479,133 B2 | 1/2009 | Sun |
| 7,480,530 B2 | 1/2009 | Sun |
| 7,615,546 B2 | 11/2009 | Gupta |
| 7,737,179 B2 | 6/2010 | Wang |
| 7,744,932 B2 | 6/2010 | Faller |
| 7,777,073 B2 | 8/2010 | Gupta |
| 7,834,210 B2 | 11/2010 | Gupta |
| 7,842,723 B2 | 11/2010 | Gupta |
| 7,886,748 B2 | 2/2011 | Boxer Wachler |
| 8,007,837 B2 | 8/2011 | Mitra |
| 8,084,063 B2 | 12/2011 | Faller |
| 8,088,364 B2 | 1/2012 | Breyfogle |
| 8,094,186 B2 | 1/2012 | Fukuoka |
| 8,097,041 B2 | 1/2012 | Barbosa |
| 8,110,207 B2 | 2/2012 | Cebrian Puche |
| 8,114,439 B2 | 2/2012 | Puig Montiel |
| 8,193,376 B2 | 6/2012 | Gupta |
| 8,211,873 B2 | 7/2012 | Gupta |
| 8,212,076 B2 | 7/2012 | Gupta |
| 8,232,417 B1 | 7/2012 | Gupta |
| 8,238,623 B2 | 8/2012 | Stephan |
| 8,278,359 B2 | 10/2012 | Southall |
| 8,298,555 B2 | 10/2012 | McCook |

(Continued)

FOREIGN PATENT DOCUMENTS

| EP | 2515652 A1 | 11/2014 |
|---|---|---|
| JP | 2007153822 A | 6/2007 |

(Continued)

OTHER PUBLICATIONS

Induchem, Unisooth EG-28, May 5, 2011 (Year: 2011).*
U.S. Appl. No. 15/098,785, filed Apr. 14, 2016, Karen Marie Osorio.
U.S. Appl. No. 15/098,804, filed Apr. 14, 2016, Karen Marie Osorio.
U.S. Appl. No. 15/099,035, filed Apr. 14, 2016, Karen Marie Osorio.
U.S. Appl. No. 15/099,065, filed Apr. 14, 2016, Karen Marie Osorio.
U.S. Appl. No. 15/099,087, filed Apr. 14, 2016, Karen Marie Osorio.
www.gnpd.com Record ID: 1748444 Eye Brightening Duo; Maybelline White Refine Mar. 2012.

(Continued)

*Primary Examiner* — Jennifer A Berrios

(74) *Attorney, Agent, or Firm* — John G. Powell

(57) ABSTRACT

A method of improving the appearance of periorbital dyschromia by identifying a target portion of skin in the periorbital region of a person that exhibits periorbital dyschromia and applying a personal care composition to the target portion of skin during a treatment period. The personal care composition includes an effective amount of Type I active, an effective amount of a Type II active, and a dermatologically acceptable carrier. The treatment period is of sufficient length for at least one of the actives to improve the appearance of the periorbital dyschromia.

7 Claims, 4 Drawing Sheets

(56) References Cited

U.S. PATENT DOCUMENTS

| | | |
|---|---|---|
| 8,329,149 B2 | 12/2012 | Lyga |
| 8,388,939 B2 | 3/2013 | Fournial |
| 8,404,648 B2 | 3/2013 | Lintner |
| 8,410,079 B2 | 4/2013 | Peter |
| 8,486,461 B2 | 7/2013 | Swanson |
| 8,507,649 B2 | 8/2013 | Lintner |
| 8,673,372 B2 | 3/2014 | Swanson |
| 8,697,656 B2 | 4/2014 | Fournial |
| 8,710,011 B2 | 4/2014 | Garcia Sanz |
| 8,744,567 B2 | 6/2014 | Fassih |
| 8,790,724 B2 | 7/2014 | Jia |
| 8,968,712 B2 | 3/2015 | Tanaka |
| 8,986,664 B2 | 3/2015 | Dicolandrea |
| 8,987,212 B2 | 3/2015 | Majeed |
| 9,050,477 B2 | 6/2015 | Fournial |
| 9,067,967 B2 | 6/2015 | García Antón |
| 9,126,060 B2 | 9/2015 | Fournial |
| 9,266,921 B2 | 2/2016 | García Antón |
| 9,333,159 B2 | 5/2016 | Hayes |
| 9,358,263 B2 | 6/2016 | Millikin |
| 9,393,266 B2 | 7/2016 | Breton |
| 9,414,970 B2 | 8/2016 | Dillon |
| 2004/0176273 A1 | 9/2004 | Bissett |
| 2007/0134174 A1 | 6/2007 | Irwin |
| 2009/0209642 A1 | 8/2009 | Gupta |
| 2009/0263435 A1 | 10/2009 | Potin |
| 2010/0130618 A1 | 5/2010 | Vaidya |
| 2010/0278765 A1 | 11/2010 | Bissett |
| 2010/0305168 A1 | 12/2010 | Robinson |
| 2010/0305169 A1 | 12/2010 | Robinson |
| 2011/0002969 A1 | 1/2011 | Serraïma |
| 2011/0020250 A1 | 1/2011 | Breyfogle |
| 2011/0033512 A1 | 2/2011 | Breyfogle |
| 2011/0158922 A1 | 6/2011 | Dupont |
| 2011/0229537 A1 | 9/2011 | Matravers |
| 2011/0229538 A1 | 9/2011 | Matravers |
| 2011/0229540 A1 | 9/2011 | Canham |
| 2011/0230566 A1 | 9/2011 | Tamargo |
| 2011/0305735 A1 | 12/2011 | Cebrian Puche |
| 2012/0034175 A1 | 2/2012 | Yarosh |
| 2012/0045405 A1 | 2/2012 | Gilman |
| 2012/0076842 A1 | 3/2012 | Fournial |
| 2012/0189569 A1 | 7/2012 | Gupta |
| 2012/0197016 A1 | 8/2012 | Laughlin, II |
| 2012/0201768 A1 | 8/2012 | Swanson |
| 2012/0283235 A1 | 11/2012 | McCook |
| 2013/0064876 A1 | 3/2013 | Viladot Petit |
| 2013/0216596 A1 | 8/2013 | Viladot Petit |
| 2013/0302261 A1 | 11/2013 | Courtois |
| 2013/0309332 A1 | 11/2013 | Fournial |
| 2013/0315650 A1 | 11/2013 | Cassin |

FOREIGN PATENT DOCUMENTS

| | | | |
|---|---|---|---|
| JP | 2009029749 A | | 2/2009 |
| JP | 2009120545 A | | 6/2009 |
| WO | WO2009132585 A1 | | 11/2009 |
| WO | WO2010082177 A3 | | 7/2010 |
| WO | WO2011042076 A8 | | 4/2011 |
| WO | WO2011125040 A3 | | 10/2011 |
| WO | WO2012003316 A1 | | 1/2012 |
| WO | WO2012003367 A2 | | 1/2012 |
| WO | WO2012112796 A2 | | 8/2012 |
| WO | WO2012143845 A2 | | 10/2012 |

OTHER PUBLICATIONS www.gnpd.com Record ID: 1876085 Eyes—Integral Anti-Fatigue Care; Biotherm Skin.Ergetic; Aug. 2012.
www.gnpd.com Record ID: 1888561 Lemon Brightening Eye Mask the Mask Shop Sep. 26, 2012.
www.gnpd.com Record ID: 1688932 Eye Cream Ziaja Sopot Rozswietlanie; Jan. 2012.
www.gnpd.com Record ID: 1699166 Eye Cream; éclos Age-Defying; Jan. 2012.
www.gnpd.com Record ID: 1708206 Beaux Yeux Beautiful Eyes Concentrate Intensive; Laface Laboratories; Jan. 2012.
www.gnpd.com Record ID: 1709819 Eye Revive Cream; Radical Skincare; Jan. 2012.
www.gnpd.com Record ID: 1736914 Resurfacing Eye Serum; Peter Thomas Roth Laser-Free; Feb. 2012.
www.gnpd.com Record ID: 1739239 Anti-Aging Eye Cream; Marbert Anti-Aging Care NoMoreAging; Mar. 2012.
www.gnpd.com Record ID: 1739353 Eye Gel Crème; Laura Mercier Flawless Skin Tone Perfecting; Feb. 2012.
www.gnpd.com Record ID: 1741729 Eye Gel Crème; Laura Mercier Flawless Skin Tone Perfecting; Feb. 2012.
www.gnpd.com Record ID: 1743441 Vitality Eye Roll-On; No7 Beautiful Skin All Skin Types; Mar. 2012.
www.gnpd.com Record ID: 1746797 Resurfacing Eye Serum; Peter Thomas Roth Laser-Free; Feb. 2012.
www.gnpd.com Record ID: 1748914 Overnight Revitalising Eye Balm; No7 Beautiful Skin All Skin Types; Mar. 2012.
www.gnpd.com Record ID: 1750911 Eye Serum; Trish McEvoy Beauty Booster; Mar. 2012.
www.gnpd.com Record ID: 1753805 Mint Cooling Eye's Cream SPF 30/PA++; Etude House; Mar. 2012.
www.gnpd.com Record ID: 1770873 Age Defy Eye Cream; Sephora Anti-Age; May 2012.
www.gnpd.com Record ID: 1771293 Illuminating Eye Contour; Polåar Cryovital Supra Vitamin; Apr. 2012.
www.gnpd.com Record ID: 1781377 Dark Circle Eye Cream; Swanson Cosmetic Science; May 2012.
www.gnpd.com Record ID: 1782294 Concentrate Eye; Ampleur Luxury White; Apr. 2012.
www.gnpd.com Record ID: 1782481 De-Puffing Eye Roll-On; Boots Time Delay Anti-Ageing Youth Maintain; May 2012.
www.gnpd.com Record ID: 1783244 DNA iQuad Infusion Total Eye Complex; SilDerm Anti-Ageing Celfix Cosmeceuticals; May 2012.
www.gnpd.com Record ID: 1789617 Eye Revive Cream; Radical skincare; May 2012.
www.gnpd.com Record ID: 1799217 Cooling Eye Roll-On; Douglas Men's System; Jun. 2012.
www.gnpd.com Record ID: 1805329 Eye' M Tired Massaging Trio Rollerball; Hard Candy; May 2012.
www.gnpd.com Record ID: 1805756 RevitalEyes Brightening Eye CreamLumixyl; May 2012.
www.gnpd.com Record ID: 1814410 Eye Magic Rooibos Illuminator Brush; Veld's; May 2012.
www.gnpd.com Record ID: 1812118 Firming Eye Gel Green People Skin Care Oct. 18, 2012.
www.gnpd.com Record ID: 1815054 Eye Treatment L'Oréal Revitalift Triple Power Aug. 8, 2012.
www.gnpd.com Record ID: 1818897 Eye Roll-On; L'Oréal Men Expert Hydra Energy; Sep. 2012.
www.gnpd.com Record ID: 1819829 Wake Up Eye Roll-On Malu Wilz Basic Aug. 8, 2012.
www.gnpd.com Record ID: 1821812 Moisturizing Eye Cream; Elizabeth Arden Visible Difference; Jun. 2012.
www.gnpd.com Record ID: 1841830 Light-Pearl Eye-Illuminating Youth Activating Concentrate Lancôme Génifique Yeux Aug. 16, 2012.
www.gnpd.com Record ID: 1842432 Rapid Revival Eye Roll-On; No7 Men Daily Care; Aug. 2012.
www.gnpd.com Record ID: 1843142 Cooling Eye Roll-On; L'Oréal Men Expert Hydra Energetic; Jul. 2012.
www.gnpd.com Record ID: 1845577 Eye Roll-On; Boots Botanics Men's; Boots; Aug. 2012.
www.gnpd.com Record ID: 1845710 Refreshing Eye Roll-On; Boots Botanics All Bright; Aug. 2012.
www.gnpd.com Record ID: 1846757 Moisturizing Eye Cream; Elizabeth Arden Visible Difference; Jul. 2012.
www.gnpd.com Record ID: 1846911 Hydrating Eye Cream; Boots Botanics Radiant Youth; Aug. 2012.

(56) References Cited

OTHER PUBLICATIONS www.gnpd.com Record ID: 1850214 Eye Cream; Every Man Jack; Aug. 2012.
www.gnpd.com Record ID: 1851401 Eyes—Eye Cream Dr. Pierre Ricaud Essence de Beauté Sublime Aug. 31, 2012.
www.gnpd.com Record ID: 1852215 Moisturizing Eye Cream; Elizabeth Arden Visible Difference; Jul. 2012.
www.gnpd.com Record ID: 1852216 Moisturizing Eye Cream; Elizabeth Arden Visible Difference; Jul. 2012.
www.gnpd.com Record ID: 1854635 Vitamin Eye Care Marbert Basic Care I Love Vitamins Aug. 24, 2012.
www.gnpd.com Record ID: 1855135 Brightening Eye Cream Lacvert O2 for You Aug. 13, 2012.
www.gnpd.com Record ID: 1855795 Total Replenishing Eye Cream; Nars Skin; Aug. 2012.
www.gnpd.com Record ID: 1858493 Eyes—Integral Anti-Fatigue Care; Biotherm Skin.Ergetic; Aug. 2012.
www.gnpd.com Record ID: 1861744 Activating Repairing Eye Gel Beauteous of Bright Aug. 17, 2012.
www.gnpd.com Record ID: 1864085 C Eye Cream Om Line Sep. 10, 2012.
www.gnpd.com Record ID: 1865218 Eye Gel La Prairie Biologie Marine Avancee Aug. 9, 2012.
www.gnpd.com Record ID: 1865219 Eye Gel La Prairie Advanced Marine Biology Aug. 9, 2012.
www.gnpd.com Record ID: 1865603 Eye Treatment 3Lab Super Aug. 10, 2012.
www.gnpd.com Record ID: 1865753 Instant Depuffing Eye Mask Sephora 1 Problem: 1 Solution Aug. 10, 2012.
www.gnpd.com Record ID: 1866000 Eyes—Integral Anti-Fatigue Care; Biotherm Skin.Ergetic; Aug. 2012.
www.gnpd.com Record ID: 1866425 Eye Gel La Prairie Advanced Marine Biology Aug. 13, 2012.
www.gnpd.com Record ID: 1866477 Anti-Ageing Eye Serum Murdock Nov. 5, 2012.
www.gnpd.com Record ID: 1866896 Youth Infusion Serum for Eyes Givenchy VAX'IN for Youth Aug. 14, 2012.
www.gnpd.com Record ID: 1867472 Essential Eye Corrector Gatineau Melatogenine AOX Probiotics Aug. 14, 2012.
www.gnpd.com Record ID: 1867736 Ultimate Whitening Anti-Spot Anti-Dark Circles Eye Serum Lancôme Blanc Expert Aug. 20, 2012.
www.gnpd.com Record ID: 1869614 Anti-Ageing Oxygen Eye Care Lancaster Skin Therapy Aug. 17, 2012.
www.gnpd.com Record ID: 1869668 Regard—Radiance Eye Care with Superfruit Extracts Payot My Payot Aug. 17, 2012.
www.gnpd.com Record ID: 1870427 Defining Eye Lift Clarins Lift-Affine Regard Aug. 24, 2012.
www.gnpd.com Record ID: 1870637 Total Replenishing Eye Cream; Nars Skin; Aug. 2012.
www.gnpd.com Record ID: 1870638 Total Replenishing Eye Cream; Nars Skin; Aug. 2012.
www.gnpd.com Record ID: 1871917 Eyes Dark Circle Corrector Clinique Even Better Aug. 20, 2012.
www.gnpd.com Record ID: 1872933 Light-Pearl Eye-Illuminating Youth Activating Concentrate Lancôme Génifique Yeux Aug. 24, 2012.
www.gnpd.com Record ID: 1872934 Light-Pearl Eye-Illuminating Youth Activating Concentrate Lancôme Génifique Yeux Aug. 24, 2012.
www.gnpd.com Record ID: 1873089 Intelligent Dark Circles Eraser Skin Peptoxyl Aug. 24, 2012.
www.gnpd.com Record ID: 1873349 Eye Treatment 3Lab Super Aug. 21, 2012.
www.gnpd.com Record ID: 1873855 Eyes Dark Circle Corrector Clinique Even Better Aug. 22, 2012.
www.gnpd.com Record ID: 1876107 Eye Crème Estée Lauder Re-Nutriv Intensive Age-Renewal Sep. 18, 2012.
www.gnpd.com Record ID: 1877479 Eye Contour Cream Avon Renew Genics Sep. 26, 2012.
www.gnpd.com Record ID: 1877640 Cucumber Cooling Eye Roll-on Essence My Skin Sep. 7, 2012.
www.gnpd.com Record ID: 1879998 Eyes—Eye Cream Dr. Pierre Ricaud Essence de Beauté Sublime Aug. 31, 2012.
www.gnpd.com Record ID: 1880552 Eyes—Integral Anti-Fatigue Care; Biotherm Skin.Ergetic; Aug. 2012.
www.gnpd.com Record ID: 1882949 Eye Roll-On Thalgo Collagene Oct. 9, 2012.
www.gnpd.com Record ID: 1882987 Miracle Eye Contour Anti-Wrinkle Cream Anne Semonin Nov. 5, 2012.
www.gnpd.com Record ID: 1884427 Eye Gel La Prairie Advanced Marine Biology Sep. 7, 2012.
www.gnpd.com Record ID: 1884497 Total Replenishing Eye Cream; Nars Skin; Sep. 2012.
www.gnpd.com Record ID: 1884654 Anti-Dark Circles Eye Cream Shiseido Oct. 19, 2012.
www.gnpd.com Record ID: 1885587 Eye Cream Shang Ji Quan Rejuvenating Collagenic Series Sep. 25, 2012.
www.gnpd.com Record ID: 1888495 Anti-Fatigue Eye Smoothing Roll-On Yves Rocher Cure Solutions Sep. 25, 2012.
www.gnpd.com Record ID: 1885901 Hydra-Cool Eye Mask Avon Naturals Aloe Sep. 20, 2012.
www.gnpd.com Record ID: 1886690 Eye Gel Collagen by Watsons Hydrating & Firming Sep. 25, 2012.
www.gnpd.com Record ID: 1887543 Wine Eye Therapy Cute Press Oct. 8, 2012.
www.gnpd.com Record ID: 1888300 Rapid Revival Eye Roll-On; Oct. 2012.
www.gnpd.com Record ID: 1888754 Wake Up! Eye Roll on Hildegard Braukmann Sep. 27, 2012.
www.gnpd.com Record ID: 1889743 Daily Eye Corrector Laboratoires Vichy ProEVEN Oct. 4, 2012.
www.gnpd.com Record ID: 1890346 Wake-Up Eye Roller Avon Solutions Vibes Oct. 12, 2012.
www.gnpd.com Record ID: 1890417 Instant Eye Rescue Eysilix Oct. 19, 2012.
www.gnpd.com Record ID: 1893571 Cucumber Cooling Eye Roll-on Essence My Skin Oct. 15, 2012.
www.gnpd.com Record ID: 1893875 Le Regard Céleste Youthful Eye Contour Les Anges Ont La Peau Douce Nov. 12, 2012.
www.gnpd.com Record ID: 1894874 Eyes—Eye Contour Care Eau Thermale Avène Rétrinal Nov. 19, 2012.
www.gnpd.com Record ID: 1900187 Eye—Lifting and Firming Eye Cream Lancôme Rénergie Lift Multi-Action Oct. 25, 2012.
www.gnpd.com Record ID: 1902190 Reviving Eye Cream GiGi Antioxidant Skin Care Oct. 17, 2012.
www.gnpd.com Record ID: 1905720 Anti-Dark Circle Brightening Eye Essence Pro-X by Olay Professional White Oct. 11, 2012.
www.gnpd.com Record ID: 1906353 Eye Contour Stick; Equilibra Aloe; Oct. 2012.
www.gnpd.com Record ID: 1907747 Eye Roll-On Thalgo Collagen Oct. 11, 2012.
www.gnpd.com Record ID: 1907789 Eye Cream Night Kanebo Freeplus Refreshing Oct. 12, 2012.
www.gnpd.com Record ID: 1908019 Eye Clear Mask Kanebo Freeplus Refreshing Oct. 12, 2012.
www.gnpd.com Record ID: 1909028 Line Reducing Eye Cream Babor Men Nov. 6, 2012.
www.gnpd.com Record ID: 1909792 Apple Anti-Tiredness Eye Care DR Docteur Renaud Soin Lissant Oct. 29, 2012.
www.gnpd.com Record ID: 1910738 Wake-Up Eye Roller Avon Solutions Vibes Oct. 12, 2012.
www.gnpd.com Record ID: 1913488 Rejuvenating Eye Pre-Essence; L'Oréal Youth Code; Oct. 2012.
www.gnpd.com Record ID: 1914098 Eye Contour Treatment Cream Avon Anew Genics Nov. 1, 2012.
www.gnpd.com Record ID: 1914282 Eye Serum Mask Boots Collagenese Nov. 6, 2012.
www.gnpd.com Record ID: 1914731 Renewal Eye Serum Vinceré Nov. 12, 2012.
www.gnpd.com Record ID: 1915295 Home Treatment Concept Brighten Up! Eye Massager Home Secrets Nov. 13, 2012.

(56) References Cited

OTHER PUBLICATIONS www.gnpd.com Record ID: 1915584 Eye Cream Revlon Absolute White+ Oct. 24, 2012.
www.gnpd.com Record ID: 1916848 Ultra Sensitive Eye Cream Artdeco Pure Minerals Skin Solutions Oct. 22, 2012.
www.gnpd.com Record ID: 1917325 Luxury Eye Cream-Serum SPF 15 Eveline Cosmetics Diamonds & 24K Gold Nov. 6, 2012.
www.gnpd.com Record ID: 1917516 2 in 1 Nourishing Eye Cream and Anti-Wrinkle Serum AA Skin Future Nov. 6, 2012.
www.gnpd.com Record ID: 1917807 Anti-Dark Circles Eye Cream Shiseido Oct. 23, 2012.
www.gnpd.com Record ID: 1919273 Eye Cream Enprani Premier Collagen Nov. 19, 2012.
www.gnpd.com Record ID: 1921582 Line Erasing Eye Cream Cute Press Juvena White Nov. 9, 2012.
www.gnpd.com Record ID: 1921687 Puffiness Fade Away Eye Mask Scentio Nov. 9, 2012.
www.gnpd.com Record ID: 1922004 Eye Cream Olay Total Effects 7 in One Antivozrastnoy Nov. 2, 2012.
www.gnpd.com Record ID: 1924745 Ultra Luminous Eye Mask Pond's Flawless White Nov. 6, 2012.
www.gnpd.com Record ID: 1927027 Miracle Eye Contour Anti-Wrinkle Cream Anne Semonin Nov. 5, 2012.
www.gnpd.com Record ID: 1939153 Overnight Revitalising Eye BalmBoots Dec. 5, 2012.
www.gnpd.com Record ID: 1937207 Hi Rise Rejuvenating Eye Elixir Orico Dec. 21, 2012.
www.gnpd.com Record ID: 1947531 Wake Up Eye Roller Avon Solutions Vibes Avon Dec. 21, 2012.
www.gnpd.com Record ID: 1881309 Eye Lift Concentrate H2O+ Aquafirm+ Dec. 20, 2012.
www.gnpd.com Record ID: 1881313 Micro-Collagen Eye Cream H2O+ Aquafirm+ Dec. 20, 2012.
www.gnpd.com Record ID: 1950138 Eye Contour Balm Oriflame Aqua-Rhythm Oriflame Dec. 19, 2012.
www.gnpd.com Record ID: 1953364 Eye Cream Juvena Master Caviar Juvena Marlies Möller Dec. 20, 2012.
www.gnpd.com Record ID: 1959286 Instant Radiance Eye Patch Annayake Ultratime Annayaké Dec. 19, 2012.
www.gnpd.com Record ID: 1960062 De-Stressing Eye Roll-On Sothys Homme Sothys Dec. 18, 2012.
www.gnpd.com Record ID: 1961968 Wrinkle Correction Eye Cream Givenchy Smile'n Repair Wrinkle Expert Parfums Givenchy Dec. 20, 2012.
www.gnpd.com Record ID: 1934504 Pueraria Wrinkle Fighting Eye Contour Giffarine Giffarine Skyline Laboratory and Health Care Nov. 20, 2012.
www.gnpd.com Record ID: 1934457 Eye Gel Watsons Water 360° Spring Water Central Watson Nov. 20, 2012.
www.gnpd.com Record ID: 1924012 Eye Gel Organic Surge Nov. 20, 2012.
www.gnpd.com Record ID: 1921661 Collagen-HYA Eye Serum Giffarine Abalone Giffarine Skyline Laboratory and Health Care Nov. 20, 2012.
www.gnpd.com Record ID: 1921555 Eye Cream Cute Press White Complete Schizo Yeast SSUP Bangkok 1991 Nov. 20, 2012.
www.gnpd.com Record ID: 1936236 Translucent Whitening Eye Cream Yue Sai Brighten Angelica L'Oréal Nov. 21, 2012.
www.gnpd.com Record ID: 1924756 Anti-Wrinkle Eye Cream SPF 10 Eveline Cosmetics Koenzymy Mlodosci Q10 Plus R Kwas Hialuronowy Nov. 21, 2012.
www.gnpd.com Record ID: 1922187 Eye Shot Anti-Fatigue Massager Care Biotherm Homme High Recharge Nov. 21, 2012.
www.gnpd.com Record ID: 1928820 Eye Contour Cien Gold Lidl Nov. 22, 2012.
www.gnpd.com Record ID: 1928490 Spectacular Lift Eye Contour Treatment Dr. Pierre Ricaud Intervention Express Nov. 23, 2012.
www.gnpd.com Record ID: 1921122 Advanced Eye Crème Laboratoire Remède Alchemy Nov. 23, 2012.
www.gnpd.com Record ID: 1915467 Liquid Red Light Eye lift Lotion DERMAdoctor Photo Dynamic Therapy Nov. 23, 2012.
www.gnpd.com Record ID: 1959660 Lifting Firming Anti-Wrinkle Eye Cream Lancôme Rénergie Yeux Multi Lift Nov. 26, 2012.
www.gnpd.com Record ID: 1932919 Eye Contour Care Uriage Eau Thermale AquaPRÉCIS Laboratoires Dermatologiques Uriage Nov. 27, 2012.
www.gnpd.com Record ID: 1936684 Energising Eye Roller Swiss Rituel Men's Expert Nov. 28, 2012.
www.gnpd.com Record ID: 1934595 Instant Depuffing Eye Mask Sephora 1 Problem: 1 Solution Nov. 28, 2012.
www.gnpd.com Record ID: 1933239 Eye Contour Cream Bio Beauté by Nuxe Laboratoire Nov. 28, 2012.
www.gnpd.com Record ID: 1943512 Eye Crème Estée Lauder Re-Nutriv Rénovatrice Anti-Rides Intensive Estée Lauder Nov. 29, 2012.
www.gnpd.com Record ID: 1881320 Eye Defense Fortifying Serum H2O+ Sea Results Dec. 3, 2012.
www.gnpd.com Record ID: 1881316 Eye Mender Plus H2O+ Sea Results Dec. 3, 2012.
www.gnpd.com Record ID: 1880906 Eye Cream Oriflame Time Reversing SkinGenist Dec. 3, 2012.
www.gnpd.com Record ID: 1947966 Light-Pearl Eye-Illuminating Youth Activator Lancôme Génifique Yeux Dec. 4, 2012.
www.gnpd.com Record ID: 1940062 Eye Essence Dr. Magic Purification + Energy Rose Brightening Shenzhen Univinson Cosmetics Dec. 4, 2012.
www.gnpd.com Record ID: 1937507 Supple Eye Gel Pechoin Baiqueling Dail Products Dec. 4, 2012.
www.gnpd.com Record ID: 1949168 Instant Lift Agent for Eye Glycel Hydro Firm Glycel Laboratoire Dec. 5, 2012.
www.gnpd.com Record ID: 1939599 Cooling Eye Roll-On Superdrug Optimum Dec. 5, 2012.
www.gnpd.com Record ID: 1938778 Precision Eye Cream L'Oréal Revitalift Laser Renew Dec. 5, 2012.
www.gnpd.com Record ID: 1931734 Active 7 Radiant Eye Gel REN Active Skincare Dec. 5, 2012.
www.gnpd.com Record ID: 1851001 Fundamental Eye Cream Yves Rocher Anti-Age Global Dec. 10, 2012.
www.gnpd.com Record ID: 1951004 Active 7 Radiant Eye Gel REN Active Skincare Dec. 11, 2012.
www.gnpd.com Record ID: 1948452 Eye Mender Plus H2O+ Sea Results Dec. 11, 2012.
www.gnpd.com Record ID: 1948410 Eye Defense Fortifying Serum H2O+ Sea Results H2O Plus Dec. 11, 2012.
www.gnpd.com Record ID: 1937827 Volu-Firm Eye Renewal Cream Mary Kay TimeWise Repair Dec. 11, 2012.
www.gnpd.com Record ID: 1955410 Volu-Firm Eye Renewal Cream Mary Kay TimeWise Repair Dec. 12, 2012.
www.gnpd.com Record ID: 1953379 Eye Gel Boots Essentials Cucumber Boots Dec. 12, 2012.
www.gnpd.com Record ID: 1944760 Whitening Crystal Eye Patches for Dark Pouches Dr. Morita Morita Roberta Healthy Biotech Dec. 12, 2012.
www.gnpd.com Record ID: 1955450 Anti-Shadow Eye Care Nivea Visage Aqua Sensation Beiersdorf Dec. 14, 2012.
www.gnpd.com Record ID: 1947465 Eye Concentrate Kiehl's Midnight Recovery Kiehl's Dec. 14, 2012.
www.gnpd.com Record ID: 1943877 Anti-Wrinkle Eye Contour Care Neo STEM Prenyl B Laboratoire Dec. 14, 2012.
www.gnpd.com Record ID: 1931492 Eye Me Up Eye Lifting Cream Along Came Betty Tesco Dec. 14, 2012.
www.gnpd.com Record ID: 1916875 24h Eye Care DM Balea Men Lift Effect DM Drogerie Markt Dec. 14, 2012.
www.gnpd.com Record ID: 1956417 Refreshing & Energising Moisturising Eye Mask Watsons Watsons Personal Care Stores Dec. 17, 2012.
www.gnpd.com Record ID: 1954688 Intensive Eye Cream Les Cosmétiques Age Science Intensive Restore Carrefour Dec. 17, 2012.
www.gnpd.com Record ID: 1940289 Instant Radiance Eye Patch Annayake Ultratime Annayaké Dec. 17, 2012.

(56) References Cited

OTHER PUBLICATIONS www.gnpd.com Record ID: 1960123 Perfect Hydration Eye Care Biodroga MD Moisture Biodroga Dec. 18, 2012.
www.gnpd.com Record ID: 1960120 Collagen Boost Eye Care Biodroga MD Anti-Age Biodroga Dec. 18, 2012.
www.gnpd.com Record ID: 1818823 Eye Gel Pads DM Balea Beauty Effect Jul. 17, 2012.
www.gnpd.com Record ID: 1830272 Eye Lift Pads Jean d'Arcel Renovar Phyto StemCell Aug. 8, 2012.
www.gnpd.com Record ID: 1831507 Eye Care Roll-On Marbert Basic Care Daily Care Aug. 8, 2012.
www.gnpd.com Record ID: 1831972 Perfect Hydration Eye Care Biodroga MD Moisture Aug. 7, 2012.
www.gnpd.com Record ID: 1834041 Eye Stick Oriflame Optimals Oxygen Boost Jul. 12, 2012.
www.gnpd.com Record ID: 1834479 Brightening Eye Contour Cream Avon Solutions Banishing Jul. 17, 2012.
www.gnpd.com Record ID: 1834855 Eye Contour Gel Armand Dupree Jul. 17, 2012.
www.gnpd.com Record ID: 1835006 Eye Contour Softening Gel Avon Solutions Hydra Jul. 13, 2012.
www.gnpd.com Record ID: 1835308 Eye Contour Restoring Cream SPF 20 Avon Solutions Ageless Jul. 17, 2012.
www.gnpd.com Record ID: 1836925 Eye Cream L'Oréal RevitaLift Laser Renew Jul. 18, 2012.
www.gnpd.com Record ID: 1837930 Eye Make-Up Remover Decléor Aroma Cleanse Jul. 23, 2012.
www.gnpd.com Record ID: 1841144 Eyes Dark Circle Corrector Clinique Even Better Jul. 31, 2012.
www.gnpd.com Record ID: 1842418 Eye Cream No7 Men Anti-Ageing Protect & Perfect Aug. 3, 2012.
www.gnpd.com Record ID: 1842438 Eye Cream No7 Protect & Perfect Intense Jul. 16, 2012.
www.gnpd.com Record ID: 1842684 Eye Roll-On Nivea for Men Skin Energy Q10 Instant Effect Jul. 24, 2012.
www.gnpd.com Record ID: 1842922 Complete Anti-Ageing Eye Roll-On L'Oréal Men Expert Vita Lift 5 Jul. 24, 2012.
www.gnpd.com Record ID: 1844422 Hydro Care Roll-On Eye Gel Ombia Cosmetics Jul. 20, 2012.
www.gnpd.com Record ID: 1844916 Eye Shot Instant Anti-Fatigue Cold Massager Gel Biotherm Homme High Recharge Jul. 27, 2012.
www.gnpd.com Record ID: 1845351 Multi-Perfection Eye Treatment Oriflame Diamond Cellular Jul. 27, 2012.
www.gnpd.com Record ID: 1845376 Anti-Shadow Eye Cream Nivea Visage Aqua Sensation Jul. 31, 2012.
www.gnpd.com Record ID: 1845703 Energetic Eye Lift Pharma Pure Jul. 30, 2012.
www.gnpd.com Record ID: 1845950 Roll-On Eye Serum Innisfree Forest for Men Jul. 27, 2012.
www.gnpd.com Record ID: 1847393 Brightening Eye Gel Elizabeth Arden Visible Difference Jul. 20, 2012.
www.gnpd.com Record ID: 1847857 60+ Restorative Anti-Signs Eye Cream O Boticário Active Genes Aug. 2, 2012.
www.gnpd.com Record ID: 1849091 Multi-Perfection Eye Tretment Oriflame Diamond Cellular Aug. 3, 2012.
www.gnpd.com Record ID: 1849268 Eye Roll-On Laboratoires Vichy Aqualia Thermal Jul. 24, 2012.
www.gnpd.com Record ID: 1850057 Brightening Eye Gel Elizabeth Arden Visible Difference Jul. 20, 2012.
www.gnpd.com Record ID: 1850063 Brightening Eye Gel Elizabeth Arden Visible Difference Jul. 20, 2012.
www.gnpd.com Record ID: 1850953 Eye System Avon Anew Ultimate 7S Aug. 3, 2012.
www.gnpd.com Record ID: 1851494 Instant Depuffing Roll-On Gel Sephora Men Aug. 6, 2012.
www.gnpd.com Record ID: 1852506 Brightening Eye Cream Avon Solutions Perfect Tone Aug. 1, 2012.
www.gnpd.com Record ID: 1852552 Vita B3 Eye Concentrate Molton Brown Skincare Jul. 24, 2012.
www.gnpd.com Record ID: 1853031 Moisturising Eye Contour Gel-Cream Méthode Jeanne Piaubert l'Hydro-Active 24 Heures Jul. 25, 2012.
www.gnpd.com Record ID: 1853379 Spectacular Lift Eye Contour Treatment Dr. Pierre Ricaud Intervention Express Jul. 25, 2012.
www.gnpd.com Record ID: 1853568 Hydra-EyeZone Eye Contour Cream Rexaline Hyper-Hydrating Rejuvenating Jul. 25, 2012.
www.gnpd.com Record ID: 1800520 Relaxing Anti-Fatigue Eye Gel-Cream Dr. Pierre Ricaud Regard Jeunesse Jul. 4, 2012.
www.gnpd.com Record ID: 1807825 Brightening Eye Cream AA Technologia Wieku 40+ Multi Regeneracja Jul. 3, 2012.
www.gnpd.com Record ID: 1809228 24h Eye Cream DM Balea Men Power Effect Jun. 29, 2012.
www.gnpd.com Record ID: 1812878 Eye Serum StemCellution Harley Street Skin Care Jun. 22, 2012.
www.gnpd.com Record ID: 1813114 Instant Depuffing Roll-On Gel Sephora Men Jul. 4, 2012.
www.gnpd.com Record ID: 1817129 Firming Eye Contour Cream Oriflame Royal Velvet Jun. 21, 2012.
www.gnpd.com Record ID: 1819931 Eye Contour Softening Gel Avon Solutions Hydra Jun. 23, 2012.
www.gnpd.com Record ID: 1820548 Under Eye Repair Crème Recova 360° Age Defying+ Fairness Jun. 20, 2012.
www.gnpd.com Record ID: 1823725 Concentrated Illuminating Eye Cream SPF 8 Eveline Cosmetics BioHyaluron 4D Jul. 2, 2012.
www.gnpd.com Record ID: 1823767 Instant Depuffing Eye Mask Sephora 1 Problème > 1 Solution Jun. 25, 2012.
www.gnpd.com Record ID: 1825271 Advanced Rejuvenating Eye Concentrate Gatineau Melatogenine AOX Probiotics Plus Jun. 21, 2012.
www.gnpd.com Record ID: 1825351 Essential Eye Corrector Gatineau Melatogenine AOX Probiotics Jun. 21, 2012.
www.gnpd.com Record ID: 1825552 Brightening Eye Roll-On Miss Hoshino Jun. 22, 2012.
www.gnpd.com Record ID: 1826338 Deep Eye Cream Chando Men Men's Skin Revitalizing Jul. 5, 2012.
www.gnpd.com Record ID: 1827490 Eye System Avon Anew Ultimate 7S Jun. 28, 2012.
www.gnpd.com Record ID: 1827880 Crystal Eye Mask MakeyStyle Jul. 6, 2012.
www.gnpd.com Record ID: 1828269 Eye Brightening Essence Skinz UV White Radiant-Gene Activator Jul. 6, 2012.
www.gnpd.com Record ID: 1829079 Soothing Eye Treatment Avon Planet Spa Greek Seas Jun. 28, 2012.
www.gnpd.com Record ID: 1830799 Active Lustrous Eye Essence LotionThe Feast of Annunciation Moistening Series Jun. 28, 2012.
www.gnpd.com Record ID: 1831368 Moisturizing Lifting Eye Serum Sulwhasoo Hydro-Aid Jun. 28, 2012.
www.gnpd.com Record ID: 1836246 Eye Cream Beautrio Extreme Firming Jul. 9, 2012.
www.gnpd.com Record ID: 1840602 Vita B3 Eye Concentrate Molton Brown Skincare Jul. 10, 2012.
www.gnpd.com Record ID: 1854144 Indulge Soothing Eye Essence Pink QQ Aug. 6, 2012.
www.gnpd.com Record ID: 1854157 Collagen Boost Eye Care Biodroga MD Anti-Age Jul. 31, 2012.
www.gnpd.com Record ID: 1859583 Azulene Soft Eye Contour Cream DR Docteur Renaud Soothing Care Aug. 6, 2012.
www.gnpd.com Record ID: 1859675 Apple Anti-Tiredness Eye Care DR Docteur Renaud Smoothing Care Aug. 6, 2012.
www.gnpd.com Record ID: 1861392 Eye Cream Burt's Bees Sensitive Aug. 6, 2012.
www.gnpd.com Record ID: 1863915 Eyes Dark Circle Corrector Clinique Even Better Aug. 8, 2012.
www.gnpd.com Record ID: 1872961 Eye Rejuvenating Serum Giorgio Armani Regenessence [3.R] Jun. 27, 2012.
www.gnpd.com Record ID: 1792552 Eye Cream Olay Total Effects 7 in One Anti-Ageing May 23, 2012.
www.gnpd.com Record ID: 1795084 P Preventive Action Anti-Dark Circles and Anti-Bags Roll-On Les Cosmètiques C Skin May 23, 2012.
www.gnpd.com Record ID: 1798148 Advanced Moisturizer Eye Cream Jean d'Arcel Hydratante Jun. 6, 2012.

(56) References Cited

OTHER PUBLICATIONS www.gnpd.com Record ID: 1799207 You Won't Believe Your Eyes Moisturising Serum Soap & Glory Jun. 6, 2012.
www.gnpd.com Record ID: 1799425 24 Hour Dual Eye Cream Avon Anew Rejuvenate May 29, 2012.
www.gnpd.com Record ID: 1799491 Anti Age Eye Contour Fluid Biodroga Institut Caviar & Radiance Jun. 6, 2012.
www.gnpd.com Record ID: 1800246 Silky Whitening Eye Mask I Love Sasatinnie May 29, 2012.
www.gnpd.com Record ID: 1800701 Micro-Vibration 3 in 1 Eye Brightener L'Oréal Dermo-Expertise White Perfect Transparent Rosy Whitening May 30, 2012.
www.gnpd.com Record ID: 1800849 Firming Eye Contour Cream Oriflame Royal Velvet May 23, 2012.
www.gnpd.com Record ID: 1801223 Eye Roll-On Nivea for Men Skin Energy Q10 Instant Effect Jun. 19, 2012.
www.gnpd.com Record ID: 1801428 Eye Cream Marks & Spencer Formula Skin Care Age Defence Jun. 12, 2012.
www.gnpd.com Record ID: 1801513 Eye Cream Marks & Spencer Formula Skin Care Age Repair Jun. 12, 2012.
www.gnpd.com Record ID: 1801563 Eye Cream Marks & Spencer Formula Skin Care Age Replenish Jun. 12, 2012.
www.gnpd.com Record ID: 1801703 Hydra-EyeZone Eye Contour Cream Rexaline Jeunesse Sur-Hydratante Jun. 15, 2012.
www.gnpd.com Record ID: 1802540 Complete Anti-Ageing Eye Roll-On L'Oréal Men Expert Vita Lift 5 Jun. 1, 2012.
www.gnpd.com Record ID: 1805093 Super-Cool De-Puffing Eye Balm Boscia May 23, 2012.
www.gnpd.com Record ID: 1806171 Eye Care 3 in 1 Marionnaud Hommes Traiter Jun. 7, 2012.
www.gnpd.com Record ID: 1806671 Garden Recipe Eye Contour Roll-On Les Cosmetiques Nectar of Nature Jun. 11, 2012.
www.gnpd.com Record ID: 1807032 Cucumber & Green Tea Eye Contour Gel Ésika Natural Care Jun. 13, 2012.
www.gnpd.com Record ID: 1808244 Firming Eye Contour Cream Oriflame Royal Velvet Jun. 12, 2012.
www.gnpd.com Record ID: 1808587 Moisture Eye Cream Juvena Skin Energy Jun. 19, 2012.
www.gnpd.com Record ID: 1808918 Euphrasia and Elder Eye Mask Arboreal Jun. 11, 2012.
www.gnpd.com Record ID: 1809453 Antiwrinkle & Firming Eye Cream Korres Black Pine Jun. 6, 2012.
www.gnpd.com Record ID: 1809997 Eye Roll-On Aqua Care Esselunga Viso Jun. 13, 2012.
www.gnpd.com Record ID: 1811770 Rejuvenating Eye Roller DG Body Jun. 14, 2012.
www.gnpd.com Record ID: 1813373 Space Defence NAC Y2 Bright Eye Lift Gel 111 Skin Dr. Y. Alexandrides MD Jun. 6, 2012.
www.gnpd.com Record ID: 1814388 First Time-Fighting Eye Contour Orlane Anagenèse 25+ May 31, 2012.
www.gnpd.com Record ID: 1818476 Anti-Fatigue Roll-On for Eyes Yves Rocher Cure Solutions Jun. 14, 2012.
www.gnpd.com Record ID: 1818983 Soothing Eye Treatment Avon Planet Spa Greek Seas Jun. 13, 2012.
www.gnpd.com Record ID: 1819845 Miracle Radiance Eye Mask Kossme Jun. 19, 2012.
www.gnpd.com Record ID: 1823253 Silky Whitening Eye Mask I Love Sasatinnie Jun. 18, 2012.
www.gnpd.com Record ID: 1824654 Eye Shot Anti-Fatigue Massager Care Biotherm Homme High Recharge Jun. 15, 2012.
www.gnpd.com Record ID: 1785725 Eye Cream Artistry Pure White Apr. 26, 2012.
www.gnpd.com Record ID: 1784941 Vita B3 Eye Concentrate Molton Brown Skincare Apr. 26, 2012.
www.gnpd.com Record ID: 1780433 Eye Treatment Olay Total Effects 7 in One Tone Correcting Apr. 26, 2012.
www.gnpd.com Record ID: 1780354 Eye Cream Line and Dark Circle Minimizing Brush Olay Total Effects 7 in One Anti-Aging Apr. 26, 2012.
www.gnpd.com Record ID: 1777515 Eye Moisturizer Neutrogena Rapid Wrinkle Repair Apr. 27, 2012.
www.gnpd.com Record ID: 1775013 Eye Cream RoC Multi Correxion Nourish Stress Repair Apr. 27, 2012.
www.gnpd.com Record ID: 1781749 Eye Fix Revitalizing Treatment glõ-therapeutics May 2, 2012.
www.gnpd.com Record ID: 1779966 Eye Cream Line & Dark Circle Minimizing Brush Olay Total Effects 7 in One Anti-Aging May 2, 2012.
www.gnpd.com Record ID: 1791609 Anti-Fatigue Smoothing Eye Roll-On Yves Rocher Cure Solutions May 3, 2012.
www.gnpd.com Record ID: 1790158 Anti-Wrinkle Eye Cream Boots Laboratories Anti-Age Serum7 Lift May 3, 2012.
www.gnpd.com Record ID: 1781842 Revitalizing Eye Gel Mask with Pearl Powder Masque*ology May 3, 2012.
www.gnpd.com Record ID: 1794288 Brightening Cream for Dark Circles Avon Solutions Banishing May 8, 2012.
www.gnpd.com Record ID: 1797787 Eyes Recovery Cream This Works Modern Natural Beauty Perfect May 9, 2012.
www.gnpd.com Record ID: 1794988 Eyes Recovery Cream This Works Modern Natural Beauty Perfect May 9, 2012.
www.gnpd.com Record ID: 1792855 Silky Whitening Eye Mask I Love Sasatinnie May 9, 2012.
www.gnpd.com Record ID: 1783383 Restorative Eye Cream H2O+ Marine CALM May 9, 2012.
www.gnpd.com Record ID: 1801270 Eye Therapy Laszlo Blue Firmarine May 14, 2012.
www.gnpd.com Record ID: 1795838 Fatigue Fighter Roll-On for Eyes Yves Rocher Cure Solutions May 14, 2012.
www.gnpd.com Record ID: 1795593 Dark Circle Eye Cream Derma e Evenly Radiant May 14, 2012.
www.gnpd.com Record ID: 1787979 Firming Eye Contour Cream Oriflame Royal Velvet May 16, 2012.
www.gnpd.com Record ID: 1791469 Eye Shot Instant Anti-Fatigue Cold Massager Gel Biotherm Homme High Recharge May 17, 2012.
www.gnpd.com Record ID: 1802466 The Eye Cream 3Lab May 18, 2012.
www.gnpd.com Record ID: 1803285 Moisturising Eye Contour Gel-Cream Méthode Jeanne Piaubert l'Hydro-Active 24 Heures May 21, 2012.
www.gnpd.com Record ID: 1793709 Eye Cream Roll-On Nivea for Men New Energy Revitalising Coenzyme Q10 May 21, 2012.
www.gnpd.com Record ID: 1766122 Wrinkle Smoother Eye Cream Physicians Formula Apr. 17, 2012.
www.gnpd.com Record ID: 1766541 Refresh Eye Gel Memotia Apr. 4, 2012.
www.gnpd.com Record ID: 1768230 Lifting Firming Anti-Wrinkle Eye Cream Lancôme Rénergie Multi-Lift Apr. 5, 2012.
www.gnpd.com Record ID: 1768589 Anti-Fatigue Eye Stick No7 for Men Apr. 17, 2012.
www.gnpd.com Record ID: 1771096 Rejuvenating Eye Roll-On Mixa Expert Peau Sensible Anti-Rides Apr. 23, 2012.
www.gnpd.com Record ID: 1771338 Anti-Puffiness Anti-Wrinkle Eye Roll-On Nivea Visage Q10 Plus Anti-Rides Apr. 20, 2012.
www.gnpd.com Record ID: 1771649 Occhi—Eye Treatment Borghese Acqua Ristorativo Apr. 12, 2012.
www.gnpd.com Record ID: 1771693 Anti-Dark Circles Eye Cream Nivea Visage Aqua Sensation Apr. 23, 2012.
www.gnpd.com Record ID: 1772527 2in1 Correcting Eye Cream Now Solutions Premium Collection Apr. 11, 2012.
www.gnpd.com Record ID: 1774097 Eye Roll-On Nivea for Men Skin Energy Q10.
www.gnpd.com Record ID: 1774452 Supple Eye Essence Pechoin Apr. 18, 2012.
www.gnpd.com Record ID: 1774472 Lifting Firming Anti-Wrinkle Eye Cream Lancôme Rénergie Multi-Lift Apr. 5, 2012.
www.gnpd.com Record ID: 1775349 Eye Cream Soap & Glory Make Yourself Youthful Apr. 18, 2012.
www.gnpd.com Record ID: 1775355 Eye Contour Treatment Ixxi Seveatherapy EliXir Apr. 16, 2012.
www.gnpd.com Record ID: 1775548 Eye Gel Algenist Firming & Lifting Apr. 12, 2012.

(56) References Cited

OTHER PUBLICATIONS www.gnpd.com Record ID: 1775570 Nurturing Eye Cream Astalift Apr. 12, 2012.
www.gnpd.com Record ID: 1776171 Lifting Firming Anti-Wrinkle Eye Cream Lancôme Rénergie Multi-Lift Apr. 11, 2012.
www.gnpd.com Record ID: 1777044 Gel for Puffy Eyes and Dark Circles Bottega Verde Apr. 17, 2012.
www.gnpd.com Record ID: 1778948 Cellcrystal Whitening Eye Cream Chcedo Snowflake Moistwhite Apr. 17, 2012.
www.gnpd.com Record ID: 1780625 Eye Complex Eve Taylor Advanced Skin Therapy Apr. 20, 2012.
www.gnpd.com Record ID: 1783458 Cucumber + Guava Firming Eye Balm the Jojoba Company Apr. 20, 2012.
www.gnpd.com Record ID: 1784434 Ava Gardner's Instant Eye Repair Erno Laszlo Hollywood Collection Apr. 24, 2012.
www.gnpd.com Record ID: 1785387 Eye Complex Eve Taylor Advanced Skin Therapy Apr. 25, 2012.
www.gnpd.com Record ID: 1788986 Vita B3 Eye Concentrate Molton Brown Skincare Apr. 26, 2012.
www.gnpd.com Record ID: 1789635 Luminescence Moisturizing Eye-Reviver Ge Givenchy Hydra Sparkling Apr. 26, 2012.
www.gnpd.com Record ID: 1803963 Perfect Eyes Cream Remedis May 22, 2012.
www.gnpd.com Record ID: 1805686 Youth Grafter SOS Eye Patch Helena Rubinstein Prodigy Powercell May 22, 2012.
www.gnpd.com Record ID: 1806735 Regard—Radiance Eye Care with Superfruit Extracts Payot My Payot May 23, 2012.
www.gnpd.com Record ID: 1807912 Dark Circles Away Collagen Eye Serum Dr. Brandt May 22, 2012.
www.gnpd.com Record ID: 1807913 Dark Circles Away Collagen Eye Serum Dr. Brandt May 22, 2012.
www.gnpd.com Record ID: 1823529 Bio-Energizing Cooling Eye Gel Eveline Cosmetics Magic of the Orchid Jul. 2, 2012.
www.gnpd.com Record ID: 1741312 Wrinkle Eye Mask Memotia Mar. 26, 2012.
www.gnpd.com Record ID: 1749398 Brightening Eye Cream SPF 15 Korres Wild Rose Mar. 20, 2012.
www.gnpd.com Record ID: 1749779 Restoring Eye Balm L'Oréal Dermo-Expertise Age Perfect Nutrition Intense Mar. 21, 2012.
www.gnpd.com Record ID: 1751059 Nourishing & Hydrating Eye CreamAA Technologia Wieku 70+ Intensywne Odzywianie Mar. 20, 2012.
www.gnpd.com Record ID: 1751251 Q10 Eye Gel Roll-On Rossmann Isana Men Mar. 20, 2012.
www.gnpd.com Record ID: 1752200 Eye Gel Superdrug Simply Pure Aqua Hydrating Mar. 27, 2012.
www.gnpd.com Record ID: 1754283 Eye Roll-On Neutrogena Hydro Boost Mar. 21, 2012.
www.gnpd.com Record ID: 1754540 Eye Gel Olay Age Defying Series Mar. 27, 2012.
www.gnpd.com Record ID: 1754943 Eye Treatment Avon Anew Genics Mar. 23, 2012.
www.gnpd.com Record ID: 1747910 Eye Roll-On Neutrogena Hydro Boost Mar. 15, 2012.
www.gnpd.com Record ID: 1748094 Whitening Intensive Eye Treatment Pure & Mild Natural Empowered White Mar. 14, 2012.
www.gnpd.com Record ID: 1748170 Eye Cream Aupres Premium Cell Renewing Mar. 13, 2012.
www.gnpd.com Record ID: 1748183 Under Eye Gel Aupres Premium Cell Renewing Mar. 13, 2012.
www.gnpd.com Record ID: 1748810 Revitalizing Eye Roll on Simple Kind to Eyes Mar. 14, 2012.
www.gnpd.com Record ID: 1749201 Revitalizing Eye Roll-On Simple Kind to Eyes Mar. 14, 2012.
www.gnpd.com Record ID: 1749475 Eye Treatment Olay Total Effects 7 in One Tone Correcting Mar. 16, 2012.
www.gnpd.com Record ID: 1749688 Restoring Eye Balm L'Oréal Dermo-Expertise Age Perfect Nutrition Intense Mar. 19, 2012.
www.gnpd.com Record ID: 1749815 Cool Eyes Anti-Wrinkle Pads Montagne Jeunesse Mar. 16, 2012.
www.gnpd.com Record ID: 1750684 Eye Cream the Body Shop Vitamin E Mar. 13, 2012.
www.gnpd.com Record ID: 1750733 Moisturising & Smoothing Eye Cream AA Technologia Wieku 30+ Energia Mlodosci Mar. 19, 2012.
www.gnpd.com Record ID: 1751313 Moisturising and Refreshing Eye Contour Gel L'Bel Hydra Calme Mar. 19, 2012.
www.gnpd.com Record ID: 1757120 Anti-Wrinkle Eye Cream Nivea Visage Vital Multi Active Soja Mar. 19, 2012.
www.gnpd.com Record ID: 1751865 Eye Contour Rescue Natural Scents Extract Mar. 20, 2012.
www.gnpd.com Record ID: 1751889 Eye Contour Cream Yves Rocher Hydra Specific White Mar. 15, 2012.
www.gnpd.com Record ID: 1752671 Youth Reviving Eye Cream Pond's Gold Radiance Mar. 13, 2012.
www.gnpd.com Record ID: 1753265 Illuminating Eye Cream La Prairie White Caviar Mar. 14, 2012.
www.gnpd.com Record ID: 1753648 Anti-Dark Circles Eye Cream Shiseido White Lucent Mar. 15, 2012.
www.gnpd.com Record ID: 1754477 Energizing Eye Serum Roll-On Chantecaille Aromacologie Nano Gold Mar. 14, 2012.
www.gnpd.com Record ID: 1754827 Anti-Aging Eye Treatment VENeffect Mar. 16, 2012.
www.gnpd.com Record ID: 1755549 Eye Contour Care Staminaline Anti-Age Mar. 27, 2012.
www.gnpd.com Record ID: 1755931 Eye Relaxing Mask Renovax Derm Linea Benessere Viso Mar. 27, 2012.
www.gnpd.com Record ID: 1756198 Nurturing Eye Cream Astalift Mar. 16, 2012.
www.gnpd.com Record ID: 1757053 Reactivating Eye Cream Babor Skinovage PX Sensational Eyes Mar. 20, 2012.
www.gnpd.com Record ID: 1757076 Cooling Eye Gel Babor Skinovage PX Sensational Eyes Mar. 20, 2012.
www.gnpd.com Record ID: 1757088 Energizing Eye Serum Roll-On Chantecaille Aromacologie Nano Gold Mar. 15, 2012.
www.gnpd.com Record ID: 1757189 Eye Balm + DR4 Lab Series Skincare for Men Treat Power Brightening Mar. 20, 2012.
www.gnpd.com Record ID: 1758382 24 Hour Dual Eye Cream Avon Anew Rejuvenate Apr. 2, 2012.
www.gnpd.com Record ID: 1759147 Spectacular Lift Eye Contour Treatment Dr. Pierre Ricaud Intervention Express Mar. 22, 2012.
www.gnpd.com Record ID: 1761402 Multi-Firming Rejuvenating Eye Balm Giorgio Armani Regenessence [3.R] High Lift Mar. 26, 2012.
www.gnpd.com Record ID: 1761669 Brightening Eye Cream SPF 15 Korres Wild Rose Mar. 22, 2012.
www.gnpd.com Record ID: 1761873 Eyes Anti-Wrinkle & Firming Care Laboratoires Vichy LiftActiv Derme Source Mar. 26, 2012.
www.gnpd.com Record ID: 1762148 Eye Cream Avon Solutions Hydra Radiance Apr. 3, 2012.
www.gnpd.com Record ID: 1762800 Anti-Wrinkle Eye Contour Care Methode Jeanne Piaubert Certitude Absolue Apr. 2, 2012.
www.gnpd.com Record ID: 1763133 Spectacular Lift Eye Contour Treatment Dr. Pierre Ricaud Intervention Express Mar. 22, 2012.
www.gnpd.com Record ID: 1764176 Eye Contour [PRO3W] Carita Progressif Anti-Rides Supreme Wrinkle Solution Mar. 23, 2012.
www.gnpd.com Record ID: 1764182 Eye Patch [PRO3W] Carita Progressif Anti-Rides Supreme Wrinkle Solution Mar. 23, 2012.
www.gnpd.com Record ID: 1764278 Energizing Eye Serum Roll-On Chantecaille Aromacologie Nano Gold Mar. 23, 2012.
www.gnpd.com Record ID: 1764742 Eye Balm + DR4 Lab Series Skincare for Men Treat Power Brightening Mar. 28, 2012.
www.gnpd.com Record ID: 1765350 Multi-Firming Rejuvenating Eye Balm Giorgio Armani Regenessence [3.R] High Lift Mar. 28, 2012.
www.gnpd.com Record ID: 1766349 Eye Contour Cream Natura Chronos Mar. 30, 2012.
www.gnpd.com Record ID: 1737633 Eye Essence Mei Ji Zhi Tan Whitening & Firming Nano Care Refining Smooth Nano Feb. 27, 2012.
www.gnpd.com Record ID: 1735253 Firming Eye Contour Cream Oriflame Royal Velvet Feb. 24, 2012.

(56) References Cited

OTHER PUBLICATIONS www.gnpd.com Record ID: 1739775 Multi-Perfector Eye Treatment Oriflame Diamond Cellular Feb. 29, 2012.
www.gnpd.com Record ID: 1740295 Eye Cream SPF 15 Tesco Vitamin E Feb. 27, 2012.
www.gnpd.com Record ID: 1740972 Eye Rescue Eye Mask with Sea Kelp Montagne Jeunesse for Men Feb. 27, 2012.
www.gnpd.com Record ID: 1741063 Double Lifting Eye L'Oréal Dermo-Expertise RevitaLift Mar. 6, 2012.
www.gnpd.com Record ID: 1741830 Hydrocapture Eye Cream Aupres Pro-Balancing Mar. 5, 2012.
www.gnpd.com Record ID: 1742013 Anti-Fatigue Ice-Effect Stick Laboratoires Vichy Aqualia Antiox Mar. 2, 2012.
www.gnpd.com Record ID: 1742220 Revitalising Eye Care Kaloderma Age Balance Feb. 28, 2012.
www.gnpd.com Record ID: 1723461 First Wrinkles Smoothing Refreshing Eye Care Galénic Nectalys Feb. 9, 2012.
www.gnpd.com Record ID: 1725826 Moisture Eye Cream M.A.C Mineralize Charged Water Feb. 9, 2012.
www.gnpd.com Record ID: 1727046 Cooling Roll-On for Eyes My Face Aloe Vera Extrakt Feb. 15, 2012.
www.gnpd.com Record ID: 1728804 Eye Gel Olay Men Solutions Multi-Solution Feb. 16, 2012.
www.gnpd.com Record ID: 1729210 Eye Contour with Argan Oil RF Triple Acción Feb. 17, 2012.
www.gnpd.com Record ID: 1730286 Eye Cream RoC Hydra+ Anti-Fatigue Feb. 17, 2012.
www.gnpd.com Record ID: 1730799 Complete Anti-Ageing Eye Roll on L'Oréal Men Expert Vita Lift 5 Feb. 22, 2012.
www.gnpd.com Record ID: 1731381 Eye Gel Olay Anti-Wrinkle Firm & Lift Feb. 9, 2012.
www.gnpd.com Record ID: 1732691 Eye Lid Serum Perricone MD Cosmeceuticals Acyl-Glutathione Feb. 16, 2012.
www.gnpd.com Record ID: 1733348 Eyes Global Anti-Wrinkle & Firming Care Laboratoires Vichy LiftActiv Derm Source Feb. 17, 2012.
www.gnpd.com Record ID: 1733779 Moisture Eye Cream M.A.C Mineralize Charged Water Feb. 10, 2012.
www.gnpd.com Record ID: 1733780 Moisture Eye Cream M.A.C Mineralize Charged Water Feb. 10, 2012.
www.gnpd.com Record ID: 1733781 Moisture Eye Cream M.A.C Mineralize Charged Water Feb. 10, 2012.
www.gnpd.com Record ID: 1734752 The Third Punch: The Eye Rejuvenator Knockout Skincare for Men Feb. 17, 2012.
www.gnpd.com Record ID: 1734815 Eye Crème Yves Saint Laurent Forever Youth Liberator Feb. 13, 2012.
www.gnpd.com Record ID: 1734817 Eye Crème Yves Saint Laurent Forever Youth Liberator Feb. 13, 2012.
www.gnpd.com Record ID: 1734923 Yeux—Intense Nutrition Eye Cream Yves Saint Laurent Temps Majeur Suprême Feb. 13, 2012.
www.gnpd.com Record ID: 1736278 Regeneration Eye Cream Elizabeth Arden Ceramide Premiere Intense Moisture and Renewal Feb. 16, 2012.
www.gnpd.com Record ID: 1737154 Eye Shot Anti-Fatigue Massager Care Biotherm Homme High Recharge Feb. 14, 2012.
www.gnpd.com Record ID: 1738708 Eye Lid Serum Perricone MD Cosmeceuticals Acyl-Glutathione Feb. 16, 2012.
www.gnpd.com Record ID: 1738709 Eye Lid Serum Perricone MD Cosmeceuticals Acyl-Glutathione Feb. 16, 2012.
www.gnpd.com Record ID: 1738775 Regeneration Eye Cream Elizabeth Arden Ceramide Premiere Intense Moisture and Renewal Feb. 16, 2012.
www.gnpd.com Record ID: 1739522 Radiance Boosting Eye Balm Boots Laboratories Dermacare Optiva Feb. 23, 2012.
www.gnpd.com Record ID: 1739880 Fine Lines Eye Cream Boots Laboratories Anti-Age Serum? Feb. 23, 2012.
www.gnpd.com Record ID: 1742316 Eye Treatment Cream Avon Anew Genics Feb. 27, 2012.
www.gnpd.com Record ID: 1743268 Eye Roll-On Bulldog Natural Skincare Original Mar. 1, 2012.
www.gnpd.com Record ID: 1744348 Eye Treatment Cream Avon Anew Genics Feb. 27, 2012.
www.gnpd.com Record ID: 1744791 Eye Treatment Cream Avon Anew Genics Feb. 27, 2012.
www.gnpd.com Record ID: 1749863 Lifting Gel Patch La Biosthetique Marcel Contier Dermosthetique Anti Age Visage Mar. 8, 2012.
www.gnpd.com Record ID: 1745324 Anti-Age Total Eye Roll-On L'Oréal Men Expert Vita Lift 5 Mar. 8, 2012.
www.gnpd.com Record ID: 1745527 Eye Lift Intense Cream Body 'Minute Skin' Minute Peau Urbaine à Mature Mar. 2, 2012.
www.gnpd.com Record ID: 1746823 Temporary Eye Tightener Peter Thomas Roth Instant FirmX Feb. 29, 2012.
www.gnpd.com Record ID: 1747187 Roll-Away—Instant Eye Fatigue Corrector Shu Uemura Red:Juvenus Mar. 6, 2012.
www.gnpd.com Record ID: 1747342 Eye Serum Kirkland Signature by Borghese Mar. 9, 2012.
www.gnpd.com Record ID: 1748251 Eye Contour Corrector Sampar Cosmakeup Glamour Shot Mar. 7, 2012.
www.gnpd.com Record ID: 1751102 Roll-Away—Instant Eye Fatigue Corrector Shu Uemura Red:Juvenus Mar. 8, 2012.
www.gnpd.com Record ID: 1753037 Lifting Gel Patch La Biosthetique Marcel Contier Dermosthetique Anti Age Visage Mar. 9, 2012.
www.gnpd.com Record ID: 1737752 It's Potent! Brightening Eye Cream BeneFit Bright Radiant Skincare Feb. 15, 2012.
www.gnpd.com Record ID: 1709371 Youth Reviving Eye Cream Pond's Gold Radiance Jan. 30, 2012.
www.gnpd.com Record ID: 1713428 Night Eye Gelly Narüko Taiwan Magnolia Brightening and Friming Feb. 1, 2012.
www.gnpd.com Record ID: 1713930 Under Eye Gel Aáranyáa Vedic Therapy Feb. 1, 2012.
www.gnpd.com Record ID: 1717433 Anti-Wrinkle Eye Essence Softto Lifting Anti-Wrinkle Series Feb. 3, 2012.
www.gnpd.com Record ID: 1717779 Eye Cream Burt's Bees Sensitive Jan. 25, 2012.
www.gnpd.com Record ID: 1717781 Eye Gel Eisker for Mummy of Gestation Period Feb. 3, 2012.
www.gnpd.com Record ID: 1718448 Micro-Vibration 3 in 1 Eye Brightener L'Oréal Dermo-Expertise White Perfect Transparent Rosy Whitening Feb. 3, 2012.
www.gnpd.com Record ID: 1720381 Eye Gel Algenist Firming & Lifting Jan. 25, 2012.
www.gnpd.com Record ID: 1721157 Under Eye Serum Fair & Lovely Multivitamin Feb. 7, 2012.
www.gnpd.com Record ID: 1722347 Gel Eye Cream Scinic Aqua EX Feb. 8, 2012.
www.gnpd.com Record ID: 1722901 Pure Lift Eye Cream Om She Advanced Botanicals Ageless Skin Feb. 7, 2012.
www.gnpd.com Record ID: 1723032 Eye Gel Algenist Raffermissant et Liftant Jan. 25, 2012.
www.gnpd.com Record ID: 1723594 Deep Hydration Anti-Ageing Eye Care Helena Rubinstein Hydra Collagenist Jan. 27, 2012.
www.gnpd.com Record ID: 1724279 Collagen Elastic Eye Essence Lanchen Aquaex Collagen Elastic Feb. 8, 2012.
www.gnpd.com Record ID: 1724873 Firming Eye Contour Cream Oriflame Royal Velvet Jan. 27, 2012.
www.gnpd.com Record ID: 1725619 Ava Gardner's Instant Eye Repair Erno Laszlo Hollywood Collection Feb. 2, 2012.
www.gnpd.com Record ID: 1725958 Eye Essence Neutrogena Clinical White Vitality Feb. 7, 2012.
www.gnpd.com Record ID: 1726246 Cucumber Cooling Eye Roll-On Essence My Skin Feb. 3, 2012.
www.gnpd.com Record ID: 1726328 Intensive Eye Care Gel Pure &Mild Soi Feb. 8, 2012.
www.gnpd.com Record ID: 1726906 Eye Shot Anti-Fatigue Massager Care Biotherm Homme High Recharge Jan. 31, 2012.
www.gnpd.com Record ID: 1727220 Masque Clarté des Yeux Express Eye-Smoothing, Lightening Mask, Dark Circles, Puffiness Payot Absolute Pure White Jan. 31, 2012.
www.gnpd.com Record ID: 1727229 Clarté des Yeux Lightening Eye Contour CreamPayot Absolute Pure White Jan. 31, 2012.
www.gnpd.com Record ID: 1728412 Riche Bio-Restorative Eye Balm Neocutis Lumière Feb. 6, 2012.

(56) References Cited

OTHER PUBLICATIONS www.gnpd.com Record ID: 1727330 Eye Lift Omorovicza Gold Jan. 31, 2012.
www.gnpd.com Record ID: 1730207 Ava Gardner's Instant Eye Repair Erno Laszlo Hollywood Collection Feb. 3, 2012.
www.gnpd.com Record ID: 1697464 Radiant Eyes Roll-On Eye Contour Serum Violetta Fabiani Jan. 19, 2012.
www.gnpd.com Record ID: 1700088 Firming Eye Contour Cream Oriflame Royal Velvet Jan. 24, 2012.
www.gnpd.com Record ID: 1700379 Eye Cream Neutrogena Rapid Wrinkle Repair Jan. 21, 2012.
www.gnpd.com Record ID: 1703302 Dark Circle Diminishing Eye Complex Narüko ampm Jan. 23, 2012.
www.gnpd.com Record ID: 1703480 Eye Gel Pure Beauty GeoAqua Ultra-Hydrating Jan. 21, 2012.
www.gnpd.com Record ID: 1704341 Anti-Fatigue Eye Treatment Aveeno Active Naturals Smart Essentials Jan. 21, 2012.
www.gnpd.com Record ID: 1706905 Bio Eye Cream Chernyy Zhemchug BioProgramma Jan. 24, 2012.
www.gnpd.com Record ID: 1711078 Q10 Eye Gel Roll-On Rossmann Isana Men Jan. 18, 2012.
www.gnpd.com Record ID: 1713370 Eye Transforming Cream Olay Total Effects 7-in-1 Anti-Ageing Jan. 17, 2012.
www.gnpd.com Record ID: 1716347 1020 Eye Contour Cream Maria Galland Mille Jan. 18, 2012.
www.gnpd.com Record ID: 1716949 Dark Circle Essence Tingmei Cross+ RE Jan. 19, 2012.
www.gnpd.com Record ID: 1717073 Eye Shot Anti-Fatigue Massager Care Biotherm Homme High Recharge Jan. 23, 2012.
www.gnpd.com Record ID: 1717552 Eye Crème Yves Saint Laurent Forever Youth Liberator Jan. 18, 2012.
www.gnpd.com Record ID: 1719078 Eyes Wide Open Instant Refreshing and Depuffing Eye Gel Philosophy Jan. 23, 2012.
www.gnpd.com Record ID: 1721681 1020 Eye Contour Cream Maria Galland Mille Jan. 23, 2012.
www.gnpd.com Record ID: 1687862 Moisturising Instant Depuffing Roll-On Gel Sephora Hidratante Jan. 12, 2012.
www.gnpd.com Record ID: 1689583 Eye Contour Care Roll-On Labell Jan. 14, 2012.
www.gnpd.com Record ID: 1690541 Every Day Eye Cream Bliss Fabulous Jan. 16, 2012.
www.gnpd.com Record ID: 1693474 Complete Anti-Ageing Eye Roll on L'Oréal Men Expert Vita Lift 5 Jan. 14, 2012.
www.gnpd.com Record ID: 1702863 Anti-Age Total Eye Roll-On L'Oréal Men Expert Vita Lift 5 Jan. 14, 2012.
www.gnpd.com Record ID: 1707023 Eye Cream Caudalíe Pulpe Vitaminée 1st Wrinkle Jan. 10, 2012.
www.gnpd.com Record ID: 1710140 Sparkle Eye Roller Olay White Radiance Jan. 13, 2012.
www.gnpd.com Record ID: 1710608 Hydra Energy Eye Roller Olay Aquaction Jan. 13, 2012.
www.gnpd.com Record ID: 1710881 Eye Contour Balm Jean d'Arcel Sensitive Jan. 13, 2012.
www.gnpd.com Record ID: 1714587 Eye Crème Yves Saint Laurent Forever Youth Liberator Jan. 17, 2012.
www.gnpd.com Record ID: 1685635 Complete Anti-Aging Eye Roll-On L'Oréal Men Expert Vita Lift 5 Jan. 4, 2012.
www.gnpd.com Record ID: 1703454 Rejuvenating Eye Remedy Shiffa Jan. 6, 2012.
www.gnpd.com Record ID: 1705299 Instant Moisture Eye Gel Lab Series Skincare for Men Treat Jan. 5, 2012.
www.gnpd.com Record ID: 1708151 Liftalize Eye-Lifting Serum Hydroxatone Jan. 10, 2012.
www.gnpd.com Record ID: 1782218 Firming Peptide Eye Cream Missha Near Skin May 8, 2012.
www.gnpd.com Record ID: 1782831 Brightening Eye Cream H2O+ Waterwhite Advanced Apr. 23, 2012.
www.gnpd.com Record ID: 1791624 Eye Recovery Balm Natura Bissé NB-Ceutical May 10, 2012.
www.gnpd.com Record ID: 1853775 Eye Lifting Serum Olay Regenerist Aug. 28, 2012.
www.gnpd.com Record ID: 1860538 Eye Moisturiser Oriental Princess Red Natural Whitening Phenomenon Aug. 24, 2012.
www.gnpd.com Record ID: 1886517 Eye Roll on Watson's Water 360° Mineral Spring Sep. 25, 2012.
www.gnpd.com Record ID: 1895176 Youth Concentrate Eye Cream Chenot GeneScience Regenage Oct. 30, 2012.
www.gnpd.com Record ID: 1896285 Eye Lifting Serum Studio 35 Beauty Oct. 16, 2012.
www.gnpd.com Record ID: 1907659 The Special Berry Firming Eye Cream Shara Shara Oct. 16, 2012.
www.gnpd.com Record ID: 1911326 Eye Crème Estée Lauder Advanced Time Zone Age Reversing Line/Wrinkle Nov. 14, 2012.
www.gnpd.com Record ID: 1915381 Total Eye Revitalizer Restructuring Lift Eye Treatment Chanel Ultra Correction Sep. 24, 2012.
www.gnpd.com Record ID: 1704144 Eye Lift Dual Eye System Cream Avon Anew Clinical Pro Jan. 3, 2012.
www.gnpd.com Record ID: 1710686 Whitening Anti-Dark Circles Eye Roller L'Egere Jan. 31, 2012.
www.gnpd.com Record ID: 1716499 Essential Eyes Eye Zone Boosting Super Serum Dior Capture Totale Jan. 16, 2012.
www.gnpd.com Record ID: 1716502 Essential Eyes Eye Zone Boosting Super Serum Dior Capture Totale Jan. 16, 2012.
www.gnpd.com Record ID: 1721459 Essential Eyes Eye Zone Boosting Super SerumDior Capture Totale Jan. 23, 2012.
www.gnpd.com Record ID: 1775105 Age Defense Eye Cream SPF 20 Clinique Superdefense Apr. 16, 2012.
www.gnpd.com Record ID: 1788134 Eye Gel Rodial Skincare Dragon's Blood May 2, 2012.
www.gnpd.com Record ID: 1790519 Intensive Anti-Wrinkle Day & Night Eye Cream SPF 8 Lirene Dermoprogram Folacin Intense 40+ May 21, 2012.
www.gnpd.com Record ID: 1792996 Eye Gel Rodial Skincare Dragon's Blood May 9, 2012.
www.gnpd.com Record ID: 1805125 Eye Gel Rodial Skincare Dragon's Blood May 17, 2012.
www.gnpd.com Record ID: 1820607 Eye Cream Innisfree Green Tea Pure Jun. 13, 2012.
www.gnpd.com Record ID: 1822042 Multi-Purpose Eye Cream Nuxe Men Jun. 18, 2012.
www.gnpd.com Record ID: 1831260 Lifting Gel Patch La Biosthetique Marcel Contier Dermosthetique Anti Age Visage Mar. 26, 2012.
www.gnpd.com Record ID: 1841529 Eye Gel Roll on Ole Henriksen Ultimate Lift Jul. 31, 2012.
www.gnpd.com Record ID: 1857325 Eye Gel Roll on Ole Henriksen Ultimate Lift Jul. 31, 2012.
www.gnpd.com Record ID: 1867456 Eye Advanced Corrective Formula HealGel Sep. 14, 2012.
www.gnpd.com Record ID: 1883334 Eye Cream Nature Republic the First Jul. 28, 2012.
www.gnpd.com Record ID: 1883372 Eye Brightener Nature Republic Aqua Super Aqua Max White C Jun. 21, 2012.
www.gnpd.com Record ID: 1734741 Multi Effect Anti-Age Eye Care Nivea Visage Vital Soy Feb. 24, 2012.
www.gnpd.com Record ID: 1739199 Complete Anti-Ageing Eye Roll on L'Oréal Men Expert Vita Lift 5 Feb. 28, 2012.
www.gnpd.com Record ID: 1742036 Eye Roll-On Laboratoires Vichy Aqualia Thermal Mar. 2, 2012.
www.gnpd.com Record ID: 1792094 Nourish Eye Cream Colbert M.D. May 1, 2012.
www.gnpd.com Record ID: 1924178 Ultra Luminous Eye Cream Pond's Flawless White Nov. 2, 2012.
Bucay V. "Adjunctive Skin Care of the Brow and Periorbital Region" Clinics in Plastic Surgery vol. 1, Issue 1, Jan. 2013, pp. 225-236.
Chantalat J, "Application of a topical biomimetic electrical signaling technology to photo-aging: a randomized, double-blind, placebo-controlled trial of a galvanic zinc-copper complex". J Drugs Dermatol. Jan. 11, 2012(1):30-7.
Kikuchi, Kumiko et al. "Imaging of hemoglobin oxygen saturation ratio in the face by spectral camera and its application to evaluate dark circles" Skin Research and Technology 2013; 19: 499-507.

(56) References Cited

OTHER PUBLICATIONS

Paolo, F, et al. "Periorbital area rejuvenation using carbon dioxide therapy" J Cosmet Dermatol. Sep. 2012;11(3):223-8 Sep. 2012.
Ranu, Harnett et al. "Periorbital Hyperpigmentation in Asians: An Epidemiologic Study and a Proposed Classification" Dermatol Surg 2011;37:1297-1303.
Raspaldo, H. et al. "Global, 3-dimensional approach to natural rejuvenation: part 1—recommendations for volume restoration and the periocular area" Journal of Cosmetic Dermatology vol. 11, Issue 4, pp. 279-289, Dec. 2012.
Sarkar, R. "Idiopathic Cutaneous Hyperchromia at the Orbital Region or Periorbital Hyperpigmentation" J Cutan Aesthet Surg. Jul.-Sep. 2012; 5(3): 183-184. Jul.-Sep. 2012.
Suh, D. "An intense-focused ultrasound tightening for the treatment of infraorbital laxity" J Cosmet Laser Ther. Dec. 2012;14(6):290-5.
Dayan SH, "Restylane persisting in lower eyelids for 5 years" J Cosmet Dermatol. Sep. 2012;11(3):237-8 Sep. 2012.
A.G.E. Eye Complex Eye Cream http://www.skinceuticals.com Sep. 29, 2016.
Lancome Vitabolic Yeux Dark Circle Eye Treatment Vitamin C Ginsen Ginkgo www.vitalmall.com Oct. 30, 2016.
Reivaderm Eyerevive Anti-Aging Eye Cream www.cal-pharma.com Oct. 30, 2016.
Gamier Skinactive Clearly Brighter Anti-Dark Circle Eye Roller www.garnierusa.com Sep. 29, 2016.
PuraLife Green Apple Eye Serum Sep. 29, 2016.
Skinstore HydroPeptide Uplifting Eye www.skinstore.com Sep. 29, 2016.
Cureherbals Dark Circle Cream www.cureherbals.com Sep. 29, 2016.
Maybelline Instant Age Rewind Eraser Treatment Makeup www.ulta.com/brent/maybelline Sep. 29, 2016.
Boots No7 Youthful Eye Serum http://us/boots.com Sep. 29, 2016.
Porcelana Night Skin Lightening Cream http://ultimarkproducts.com Sep. 29, 2016.
Essensu Organic Dark Circle Eye Cream with Haloxyl Sep. 29, 2016.

\* cited by examiner

METHOD OF IMPROVING THE APPEARANCE OF PERIORBITAL DYSCHROMIA

FIELD

The present disclosure is directed generally to a method of improving the appearance of periorbital dyschromia. More specifically, the present disclosure is directed to improving the appearance of periorbital dyschromia by applying a cosmetic composition comprising chronic actives for treating different types of periorbital dyschromia to periorbital skin in need of such treatment.

BACKGROUND

Periorbital dyschromia, which is sometimes referred to as under-eye dark circles, is generally recognized as an undesirable discoloration of the skin around the eyes, and is commonly associated with fatigue and/or aging. A variety of ways to improve the appearance of periorbital dyschromia have been devised, such as applying concealers and/or other cosmetic products to hide its appearance. But using makeup to hide the appearance of periorbital dyschromia is only a temporary solution. In order to maintain the cosmetic benefit provided by conventional makeup products, a user will typically apply the product daily and, in some instances, may even be required to reapply it throughout the day. Thus, a more permanent solution is desired to reduce and/or eliminate some of the undesirable aesthetic features commonly found around the eye, for example, by addressing the underlying causes(s) of the periorbital dyschromia.

In an effort to find a solution to the problem of periorbital dyschromia, researchers have tried to identify the underlying causes of the condition. Currently, periorbital dyschromia is recognized as a multifactorial pathogenesis that is not well elucidated. While it is generally known that there may be different types of periorbital dyschromia, there is no universally recognized definition for each type. And even among those researchers who recognize that there are different types of periorbital dyschromia, some still propose treating different types of periorbital dyschromia with a single composition or material in a "one size fits all" approach.

Accordingly, it would be desirable to provide a method of improving the appearance of periorbital dyschromia by applying a cosmetic composition comprising two or more chronic actives to a target portion of skin exhibiting periorbital dyschromia.

SUMMARY

The present disclosure provides a cosmetic composition for improving the appearance of periorbital dyschromia. The cosmetic composition comprises an effective amount of a Type I active; an effective amount of a Type II active; a dermatologically acceptable carrier; and a viscosity of from about 50,000 to about 200,000 centipoise. Also provided herein is a method of improving the appearance of periorbital dyschromia. The method comprises identifying a target portion of periorbital skin exhibiting periorbital dyschromia and applying the foregoing composition to the target portion of skin during a treatment period. The treatment period is of sufficient length for the cosmetic composition to improve the appearance of the periorbital dyschromia.

DETAILED DESCRIPTION

Figure 1:
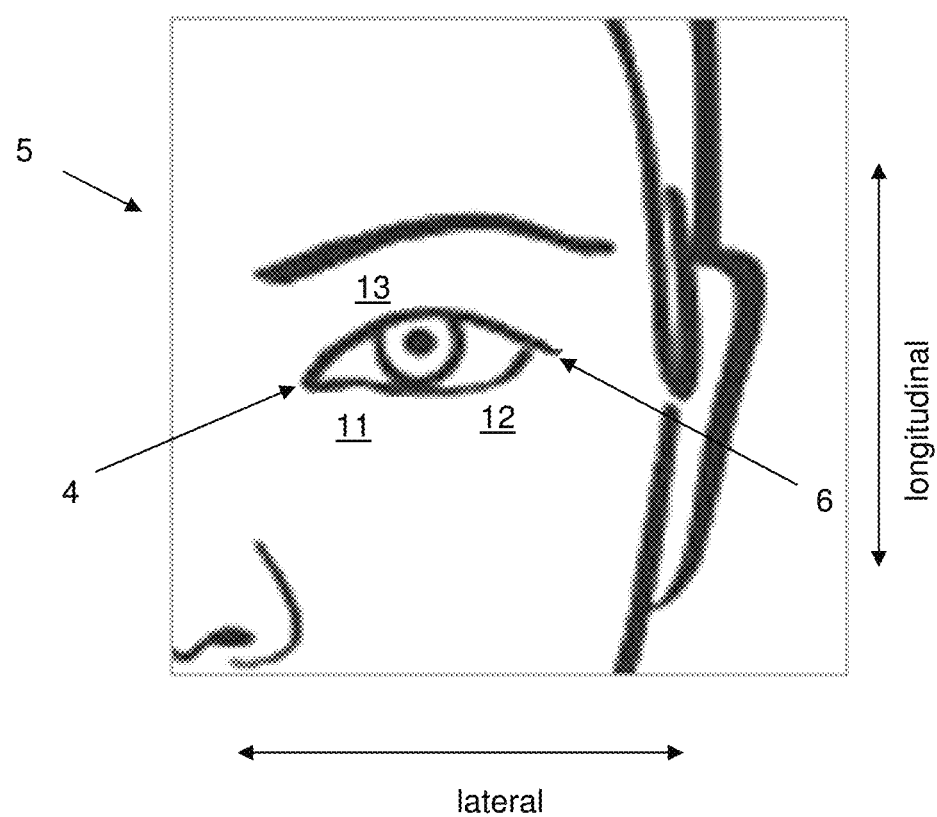
FIG. 1 is an illustration of various portions of a human face.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are weight percentages based on the weight of the composition, unless specifically stated otherwise. All ratios are weight ratios, unless specifically stated otherwise. All ranges are inclusive and combinable, are inclusive of narrower ranges, and delineated upper and lower range limits are interchangeable to create further ranges not explicitly delineated. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity.

The compositions herein can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

"Chronic active" means an active suitable for use in a topical cosmetic composition that continues to provide the desired benefit after use of the active is discontinued. Chronic actives provide a relatively long lasting cosmetic benefit as compared to the acute actives commonly found in conventional makeup products that are intended to cover or hide perceived cosmetic flaws (e.g., the pigments, dyes, lakes and other colorants commonly found in foundations and concealers). In some instances, chronic actives work via recurrent use of the active over an extended period of time (e.g., use of the active for more than 1 week). In contrast, acute actives have no lasting effect on the skin, and once the acute active is removed, the skin is the same in appearance as before the acute active was applied. Compositions containing chronic actives may be applied on the order of about once per day over such extended periods. In some instances, the application rates may vary from about once per week to about three times per day or at some rate in between. The chronic active may provide the desired benefit almost immediately, or after some minimum amount of recurring use of the composition (e.g., after 1, 2, 3, 4, 5, 6, 7, 8, 9, 19, 11, or even 12 weeks). The benefit provided by the chronic active may last for more than 1 day (e.g., more than 2, 3, 4, 5, or 6 days), more than 1 week (e.g., more than 2, 3, or 4 weeks) or even more than a month after use of the composition containing the chronic active is discontinued.

"Cosmetic" means providing a desired visual effect on an area of the human body. The visual effect may be temporary, semi-permanent, or permanent. Some non-limiting examples of "cosmetic products" include products that leave color on the face, such as foundation, mascara, concealers, eye liners, brow colors, eye shadows, blushers, lip sticks, lip balms, face powders, solid emulsion compact, and the like.

"Cosmetic agent" means any substance, as well any component thereof, suitable for use in a topical cosmetic composition intended to be contacted with (e.g., rubbed, poured, sprinkled, sprayed, introduced into, or otherwise applied to) a mammalian body or any part thereof to provide a cosmetic effect. Cosmetic agents may be chronic or acute and may include substances that are Generally Recognized as Safe (GRAS) by the US Food and Drug Administration, food additives, and materials used in non-cosmetic consumer products including over-the-counter medications.

"Cosmetic composition" means any composition comprising a cosmetic agent that is suitable for topical application to mammalian skin.

"Disposed" refers to an element being located in a particular place or position relative to another element.

"Effective amount" means an amount of a compound or composition sufficient to significantly induce a positive appearance and/or feel benefit but low enough to avoid serious side effects, i.e., to provide a reasonable benefit to risk ratio, within the scope of sound judgment of the skilled artisan. In the present method, an effective amount of a chronic active is an amount sufficient to improve the appearance of at least one type of periorbital dyschromia during a treatment period.

"Improve the appearance of" means effecting a desirable change or benefit in periorbital dyschromia appearance. For example, an improvement in the appearance of Type II or Type III periorbital dyschromia can correspond to a positive score on the Visual Perception Scale ("VPS"); a decrease in blood perfusion; an increase in L* value; a decrease in a* value and/or an increase in b* value.

"L*a*b*" refers to the commonly recognized color space specified by the International Commission on Illumination ("CIE"). The three coordinates represent the lightness of the color (L*=0 yields black and L*=100 indicates diffuse white), its position between magenta and green (a*, negative values indicate green while positive values indicate magenta) and its position between yellow and blue (b*, negative values indicate blue and positive values indicate yellow).

"Periorbital" means around the orbit of the eye. The periorbital region of a person is the area of the face generally disposed around the eye socket and typically lies between the bottom of the brow and the top of the cheek in the longitudinal direction and between the bridge of the nose and the temple in the lateral direction.

"Periorbital Dyschromia" is a condition that occurs when the tone of the skin in the periorbital region of person appears noticeably different from tone of the skin in a nearby portion of the face such as the cheek, nose, forehead, temple and/or another portion of the periorbital region. Periorbital dyschromia is generally bilateral (i.e., it occurs in the periorbital region of both sides of the face). Periorbital dyschromia may manifest as the appearance of a difference in skin tone in the periorbital region relative to other regions of the face and/or body (e.g., cheek, nose, forehead, temple, chin). Periorbital dyschromia may appear as a result of hyperpigmented or hypopigmented skin in the periorbital region. In some instances, periorbital dyschromia may be classified visually by an expert grader (i.e., someone trained to visually classify periorbital dyschromia) either in-person or from a captured image. In some instances, periorbital dyschromia may be classified visually by an expert grader (i.e., someone trained to visually classify periorbital dyschromia) either in-person or from a captured image. In some instances, periorbital dyschromia may be analyzed and/or classified using a diagnostic device configured to use an imaging technique. It may be desirable to place such diagnostic devices and/or expert graders in a retail environment, for example near cosmetic eye-care products. Type I, Type II and Type III periorbital dyschromia are described in more detail below.

"Personal care composition" means a composition suitable for topical application on mammalian keratinous tissue that provides an acute or chronic benefit to the keratinous tissue or a type of cell commonly found therein.

"Topical application" means to apply or spread the compositions of the present invention onto the surface of the keratinous tissue.

The discovery that there are different types of periorbital dyschromia with different underlying biological causes and appearances has led to a need to identify chronic actives and/or combinations of actives that can treat each of the different types of periorbital dyschromia. For example, a consumer may not which type of periorbital dyschromia they exhibit, and thus may not know which product to purchase. A variety of chronic actives that improve the appearance of a particular type or types of periorbital dyschromia have now been found. By providing a cosmetic composition that includes at least one chronic active for treating each type of periorbital dyschromia, and preferably does not worsen the appearance of another type, a user can treat periorbital dyschromia without having to ensure the correct product is selected.

Types of Periorbital Dyschromia

There are a variety of evaluation techniques suitable for identifying and/or evaluating the type of periorbital dyschromia exhibited by person (e.g., visual evaluation, blood perfusion, image analysis, histological analysis, biomarker analysis, gene expression signature analysis and/or gene expression theme analysis). In the present method, the periorbital dyschromia exhibited by a person may be classified as Type I, Type II, or Type III. Alternatively, a person may have a "No Dyschromia" condition.

FIG. 1 illustrates the periorbital region of a human face 5 divided into three zones 11, 12 and 13, which are useful for helping identify the different types periorbital dyschromia. Zone 1 11 is disposed generally in the inner portion of the under-eye area and extends laterally from the inner corner 4 of the eye to about half the distance to the outer corner 6 of the eye. Zone 2 12 extends from the distal edge of Zone 1 11 (i.e., from about the midpoint under the eye) to the outer corner 6 of the eye. Zone 1 11 and Zone 2 12 extend longitudinally from the lower eyelid to the top of the cheekbone. Zone 3 is disposed above the eye and extends laterally from the inner corner 4 of the eye to the outer corner 6 of the eye. Zone 3 13 also extends longitudinally from the top of the eye to the eyebrow.

Type I periorbital dyschromia is visually characterized by continuous discoloration of both the upper and lower eyelid skin. The discolored periorbital skin associated with Type I periorbital dyschromia typically includes substantially uniform brown, yellow and/or orange tones in the skin of the periorbital region, which may resemble the color of tanned skin or an age spot. Type I periorbital dyschromia may also be generally defined, in part, by its location in the upper and lower portions of the periorbital region (i.e., proximate the lower eyelid and the upper eyelid). In other words, Type I periorbital dyschromia is typically exhibited in Zones 1 and 3 of the periorbital region and, in some instances, Zone 2. Type II periorbital dyschromia is characterized by continuous discoloration of the lower eyelid skin. The discolored periorbital skin associated with Type II periorbital dyschromia typically includes substantially uniform purple, pink and/or bluish tones, which may resemble the color of bruised skin. Type II is generally defined, in part, by its presence in the inner, lower portion of the periorbital region (i.e., Zone 1) and its absence in the upper portion of the periorbital region (i.e., upper eyelid or Zone 3) and outer, lower portion (i.e., Zone 2). Type III periorbital dyschromia is characterized by the presence of skin tones that resemble sunburned skin. Type III is generally defined, in part, by its presence in the under-eye and above-the-eye portions of the periorbital region. A No Dyschromia condition may be visually characterized by the lack of an uneven or discontinuous skin tone in the periorbital region.

Figure 2A:
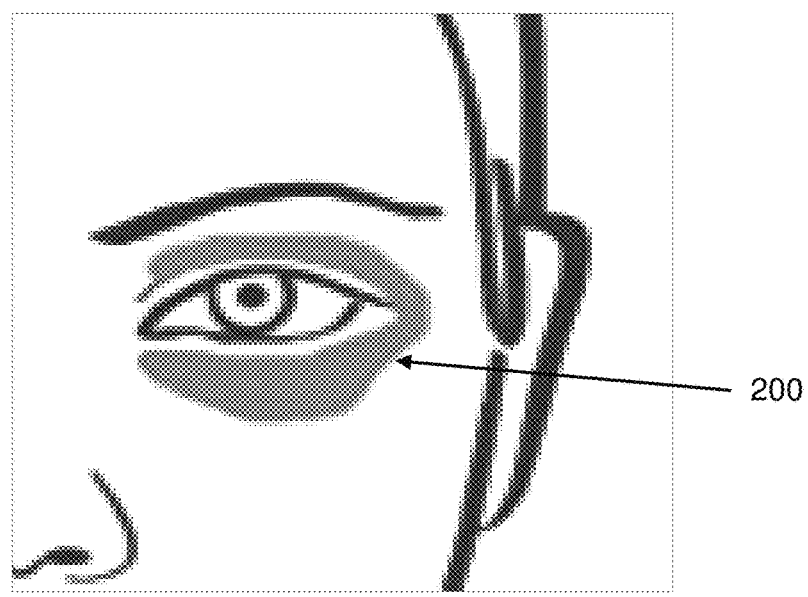
FIGS. 2A and 2B illustrate examples of the portion of the periorbital region affected by Type I periorbital dyschromia.
Figure 2B:
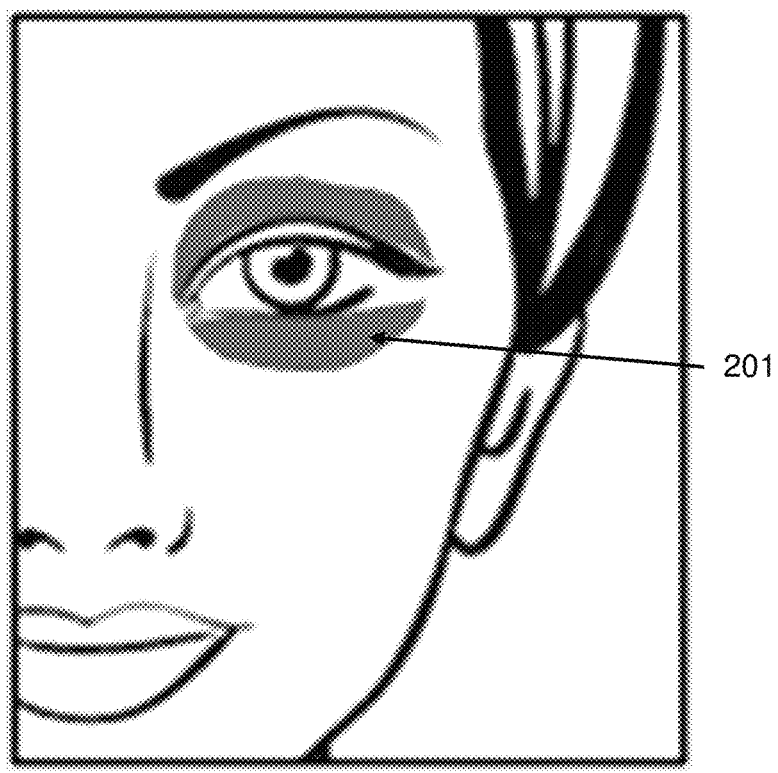
Figure 3A:
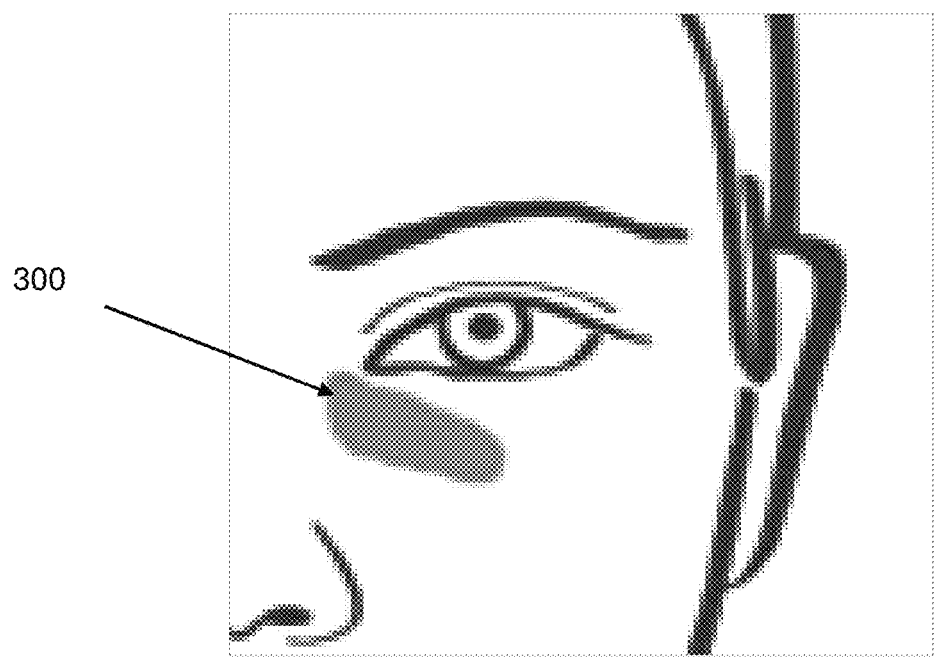
FIGS. 3A and 3B illustrate examples of portion of the periorbital region affected by Type II periorbital dyschromia.
Figure 3B:
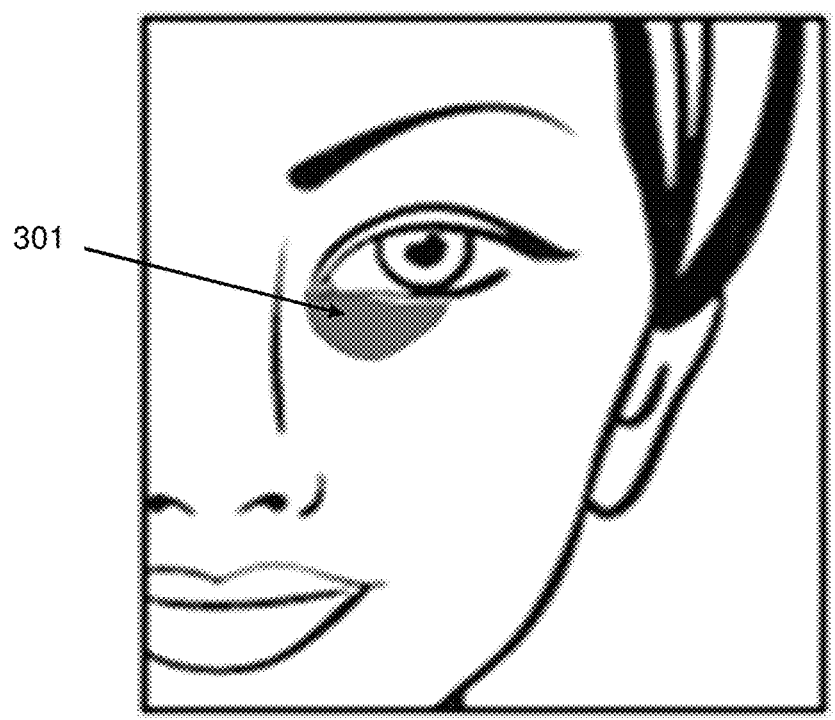
Figure 4A:
FIGS. 4A and 4B illustrate examples of portion of the periorbital region affected by Type III periorbital dyschromia.
Figure 4B:
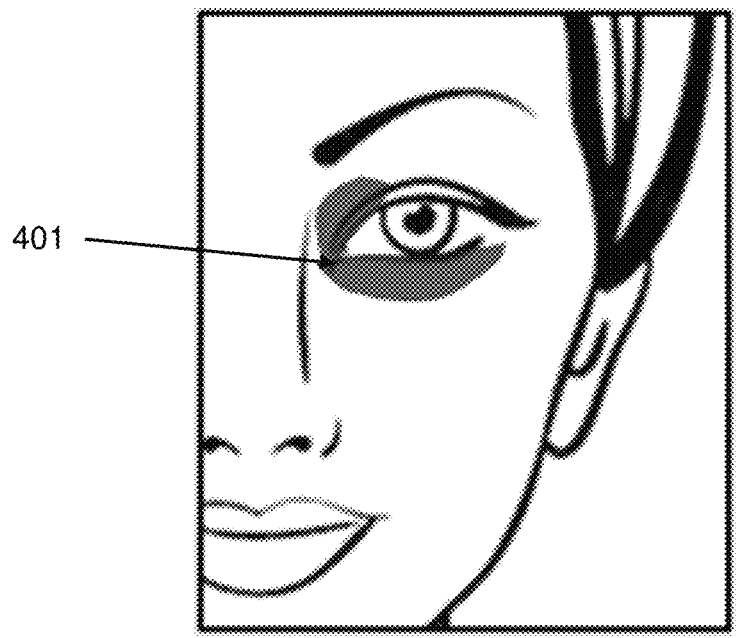

FIGS. 2A and 2B illustrate examples of Type I periorbital dyschromia, which is represented by the shaded portions 200 and 201, respectively, of the periorbital region. FIGS. 3A and 3B illustrate examples of Type II periorbital dyschromia (i.e., the shaded portions 300 and 301, respectively, of the periorbital region). FIGS. 4A and 4B illustrate examples of Type III periorbital dyschromia (i.e., the shaded portions 400 and 401, respectively, of the periorbital region). In some instances, the type of periorbital dyschromia may be identified according to the present method based on its location in the periorbital region, as illustrated in FIGS. 2A, 2B, 3A, 3B, 4A and/or 4B.

Different types of periorbital dyschromia may be distinguished from one another using known imaging techniques such as RGB color imaging. For example, Type I periorbital dyschromia may be characterized by generally having lower RGB values relative to Types II and III. Type II periorbital dyschromia may be characterized by generally having higher RGB values compared to Types I and III. Type III periorbital dyschromia may include characteristics of both Type I and Type II.

Type I, Type II and Type III periorbital dyschromia may also be distinguished from one another using histological evaluation techniques that include, for example, sectioning and staining, followed by examination under a microscope (e.g., light or electron). In particular, it has been found that the abundance and/or location of certain cellular structures (e.g., melanin) within skin biopsy samples obtained from periorbital skin may be used to distinguish Type I, Type II and Type III periorbital dyschromia from one another. For example, Type I periorbital dyschromia may be characterized by an over-abundance of melanin in the epidermis and the unexpected presence of melanin in the dermis of a skin sample. On the other hand, Type II periorbital dyschromia may characterized by an unexpected scarcity of melanin in the epidermis and an absence of melanin in the dermis. Type III periorbital dyschromia may be characterized by a combination of Type I and Type II characteristics.

In some instances, Type I, Type II and Type III periorbital dyschromia may be distinguished from one another by the scarcity and/or abundance of certain molecules in the epidermis of periorbital skin, such as pyrrole-2,3,5-tricarboxylic acid ("PTCA"), which is formed as a result of oxidative degradation of eumelanin. It has been found that Type I and Type III periorbital dyschromia have higher PTCA levels than Type II, and that Type I may exhibit higher PTCA levels than Type III.

Methods of Use

The method herein includes the topical application of a personal care composition to a target skin surface exhibiting periorbital dyschromia. The personal care composition includes a safe and effective amount of an extract of a chronic active for treating at least one type of periorbital dyschromia, i.e., an amount of the chronic active sufficient to improve the appearance of the periorbital dyschromia after a suitable course of treatment (e.g., at least 2, 4 or 8 weeks).

The target skin surface may be identified by the person exhibiting the periorbital dyschromia (e.g., via a self-assessment), an expert grader (e.g., in-person or from an image of the person), a diagnostic device in combination with a suitable diagnostic method (e.g., a digital camera in combination with suitable image analysis software), or a combination of these. For example, the method of identification may include examination of Zones 1, 2 and/or 3 of the periorbital region of a subject person and evaluating the color, location and/or intensity of the periorbital dyschromia to identify the periorbital dyschromia as a particular type (e.g., Type I, Type II, or Type III). Once the periorbital dyschromia present on the target skin surface is identified, the cosmetic composition may be applied to the target skin surface for a period of time sufficient to improve the appearance of the periorbital dyschromia. Improvements in periorbital dyschromia herein can be demonstrated by a positive VPS score (e.g., from +0.1 to +4 or any value in this range), a decrease in blood perfusion (e.g., a decrease of at least 10, 12, 14, 16, 20 or even 25); an increase in L* value (e.g., an increase of at least 0.1, 0.2, 0.3, 0.4, 0.5, 0.6, 0.7, 0.8, 0.9 or even an increase of 1 or more); a decrease in a* value (e.g., a decrease of at least 0.1, 0.2, 0.3, 0.4, 0.5, 0.6, 0.7, 0.8, 0.9 or even a decrease of 1 or more); and/or an increase in b* value (e.g., an increase of at least 0.1, 0.2, 0.3, 0.4, 0.5, 0.6, 0.7, 0.8, 0.9 or even an increase of 1 or more). Methods for determining VPS score, blood perfusion and L*a*b* values are described in more detail below.

Periorbital dyschromia may be treated according to the present method by applying a composition comprising an effective amount of a suitable chronic active to the dyschromic portion of skin about once a day, twice a day, or even more frequently during a treatment period. In some instances the composition may be applied one or more times per week but less than once per day, e.g., 2, 3, 4, 5, or 6 time per week. For example, the composition may be applied in the morning after showering, in the evening before bed and/or as part of a daily beauty regimen(s). The treatment period may last for 1 or more weeks (e.g., 2, 3, 4, 5, 6, 7 or even 8 weeks or more), multiple months (e.g., 2-12 months) or even multiple years. The treatment period should be long enough for the chronic active to improve the appearance of the periorbital dyschromia.

It may be desirable to apply the composition locally. As used herein, "localized", "local", and "locally" mean that the composition is delivered to the targeted area of skin (i.e., the target portion of periorbital skin exhibiting periorbital dyschromia) while minimizing delivery to portions of skin not requiring treatment. For example, the composition may be applied to the target skin surface in Zones 1, 2 and/or 3, depending on the type of periorbital dyschromia being treated, and lightly massaged into the target skin surface. Alternatively, the composition may be applied to the entire periorbital region or even the entire face. Alternatively, "general" or "generally", when referring to applying the composition, means applying the composition to the target area of skin and one or more additional areas of skin other than the target area (e.g., a skin care composition that is applied to the entire face including a target portion of skin in the periorbital region).

In some instances, it may be desirable to use the present composition as part of a skin care regimen. For example, a first composition that includes an effective amount of a suitable chronic active may be applied generally or locally to the skin in the periorbital regions of the face, and a second composition that includes one or more skin care agent (e.g., tone agents or moisturizers), may be applied to a portion of skin disposed outside the periorbital region (e.g., the entire face or a portion thereof). The first and second composition may be applied in any order, as desired, as long as the treatment effectiveness of the chronic active is not undesirably inhibited.

The form of the composition or the dermatologically acceptable carrier should be selected to facilitate application. In some instances, the composition may be delivered with an applicator suitable for general and/or localized application. For example, the applicator may be configured to suitably apply from 1 to 50 µL/cm$^2$ of composition to a target skin surface. Of course, it will be appreciated that applicators are not required and the personal care composition herein can also be applied directly by using one's finger or in other conventional manners.

Compositions

Compositions suitable for use in the method herein include an effective amount of at least one chronic active selected to improve the appearance of Type I periorbital dyschromia ("Type I active") disposed in a dermatologically acceptable carrier. It may be desirable to select a Type I active that does not worsen the appearance of Type II and/or Type III periorbital dyschromia. In some instances, the Type I active may also improve the appearance of Type III periorbital dyschromia. Some non-limiting examples of Type I actives include tocoquinones; panthenol; 5,5-Dimethyl-1-pyrroline N-oxide; orotic acid; amino acetic acid; cyclohexane-1,2,3,4,5,6-hexol; 8-cyclopentyl-1,3-dipropylxanthine; lactobionic acid; a mixture of propyl gallate, gallyl glucoside, and/or epigallocatechin gallatyl glucoside (e.g., UNISOOTH EG-28 from Induchem); salicylates (e.g., sodium salicylate); vitamin B3 compounds (e.g., niacinamide); undecylenoyl phenylalanine (e.g., SEPIWHITE from Seppic); a mixture of glycerin, steareth-20, n-hydroxysuccinimide, chrysin, palmitoyl tripeptide-1, and palmitoyl tetrapeptide-7 (e.g., HALOXYL from Sederma); a mixture of *Chenopodium quinoa* seed extract and butylene glycol (e.g., ADIPOLESS from Seppic); a combinations of these. The Type I active(s) may, individually or collectively, be included in a topical cosmetic composition at from 0.0001% to 15%, from 0.0002% to 10%, from 0.001% to 15%, from 0.025% to 10%, from 0.05% to 10%, from 0.05% to 5%, or even from 0.1% to 5%, by weight of the total composition.

Compositions suitable for use in the method herein include an effective amount of at least one chronic active selected to improve the appearance of Type II periorbital dyschromia ("Type II active") disposed in a dermatologically acceptable carrier. It may be desirable to select a Type II active that does not worsen the appearance of Type I and/or Type III periorbital dyschromia. In some instances, the Type II active may also improve the appearance of Type III periorbital dyschromia. Some non-limiting examples of Type I actives include pumpkin seed extract, fava bean extract, cholecalciferol, and combinations thereof. The Type II active(s) may, individually or collectively, be included in a topical cosmetic composition at from 0.0001% to 15%, from 0.0002% to 10%, from 0.001% to 15%, from 0.025% to 10%, from 0.05% to 10%, from 0.05% to 5%, or even from 0.1% to 5%, by weight of the total composition.

A particularly suitable example of a Type II active is pumpkin seed extract (INCI name: *Cucurbita pepo* Seed Extract; CAS No. 289-741-0). Pumpkin seed extract is known for use in topical skin care compositions for promoting general skin health and as a 5-α-reductase inhibitor (see, e.g., U.S. Pat. No. 8,048,456 and U.S. Pub. No. 2013/0309217), but it was not previously known that pumpkin seed extract improves the appearance of Type II periorbital dyschromia. In addition, the present studies also suggest that pumpkin seed extract improves the appearance of Type III periorbital dyschromia and does not worsen the appearance of Type I periorbital dyschromia. An example of a fava bean extract suitable for use herein is FOLLISYNC, available from Ashland Specialty Ingredients.

Another particularly suitable example of a Type II active is fava bean extract (INCI name: *Vicia Faba* Seed Extract; CAS No. 89958-06-5). Fava bean extract is known for use in promoting hair health and growth and as a skin moisturizing agent (see, e.g., U.S. Pub. No. 2013/0189381, filed by Dal Farra, et al.), but it was not previously known that fava bean extract can be used to improve the appearance of Type II periorbital dyschromia. In addition, the present studies also suggest that fava bean extract may improve the appearance of Type III and does not worsen the appearance of Type I periorbital dyschromia. An example of a pumpkin seed extract suitable for use herein is OCALINE PF, available from Soliance, France.

Pumpkin seed extract and fava bean extract may be formed as a peptidic hydrolyzate resulting from the hydrolysis of endogenous proteins. The peptidic hydrolyzate generally includes a mixture of compounds predominantly represented by peptides. The term "peptide" refers to a sequence of two or more amino acids linked by peptide bonds or modified peptide bonds; whereas the term "polypeptide" designates a larger peptide (e.g. more than four). The use of peptidic hydrolyzates, in particular low molecular weight peptidic hydrolyzates, has many advantages in cosmetics. In addition to generating compounds of peptidic nature that did not already exist in the starting protein mixture, hydrolysis and purification make it possible to provide cosmetic compositions that are more stable, more easily standardizable, and causing fewer allergic reactions.

Pumpkin seed and fava bean extract may be obtained by extracting proteins from the seeds of the plant, hydrolyzing them and then, optionally, purifying the peptide fragments. Additionally or alternatively, the proteins may be extracted from the whole plant or a specific part of the plant (leaves, stems, roots, etc.). In some instances, the proteins are extracted by crushing the seeds (or other portions of the plant) and suspending the crushed seeds in an alkaline solution containing an insoluble polyvinylpolypyrrolidone (PVPP) adsorbent (0.01-20%), which facilitates the subsequent hydrolysis and purification operations. The soluble fraction, which contains the proteins and carbohydrates, is collected after centrifugation and filtering. This crude solution is then hydrolyzed under controlled conditions to generate soluble peptides. Hydrolysis is carried out chemically and/or advantageously with proteolytic enzymes. For the removal of polyphenol substances, an amount of PVPP can be added to the reaction medium in this controlled hydrolysis step. Next, the solution is filtered to eliminate the enzymes.

In some instances, the compositions herein include an effective amount of at least one chronic active selected to improve the appearance of Type III periorbital dyschromia ("Type III active") disposed in a dermatologically acceptable carrier. It may be desirable to select a Type III active that does not worsen the appearance of Type I and Type II periorbital dyschromia. In some instances, the Type III active may also improve the appearance of Type I or Type II periorbital dyschromia. Some non-limiting examples of Type III actives include hydroxycinnamic acid, proline, and combinations thereof. The Type III active(s) may, individually or collectively, be included in a topical cosmetic composition at from 0.0001% to 15%, from 0.0002% to 10%, from 0.001% to 15%, from 0.025% to 10%, from 0.05% to 10%, from 0.05% to 5%, or even from 0.1% to 5%, by weight of the total composition.

The amount of extract that is "effective" may differ from one particular source (e.g., manufacturer) of extract to another, and can be determined by the skilled artisan based upon the particular extract product's level of activity (e.g., level of active components present). As with any extract, the concentration of active components in the particular extract product to be used will depend on factors such as the final dilution volume of the extract product, the particular extraction method employed, the natural range of variation among individual plants, and other common factors known to those skilled in the art.

Suitable cosmetic compositions may be in various product forms that include, but are not limited to, solutions, suspensions, lotions, creams, gels, toners, sticks, pencil, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks (with and without an insoluble sheet), makeup such as foundations, eye liners, and eye shadows, and the like.

In some instances, it may be important to provide a cosmetic composition that has a suitable viscosity, for example, to encourage regular use of the product. The skin in the periorbital region of a person is typically thinner and more delicate than the skin in many of other others of the face or body. If the product viscosity is too low, it may be difficult to control the application of the product to the small, delicate eye area, as the product tends to spread or run too much on the skin and may even get into the eye, potentially causing irritation. On the other hand, if the viscosity is too high, the product may drag and pull on the skin as it is spread, making it difficult to apply or even damaging or irritating the delicate periorbital skin. Accordingly, products for use herein have a viscosity between 50,000 and 200,000 cps (e.g., between 70,000 and 150,000 cps, between 90,000 and 120,000 cps, or any value in these ranges). Viscosity is determined at 20° C.±2° C. using a BROOKFIELD DV-II+ brand viscometer or equivalent with a T-C spindle at 5 rpm with a heliopath setting.

In addition, due to its proximity to the eye, it may be desirable for the present compositions to have an opacity that provides an acute benefit and/or encourages regular use of the product. For example, if the opacity of the composition is too low, it may not conceal the appearance of the periorbital dyschromia it is intended to treat. On the other hand, in this example, if the product opacity is too high, the product may suitably conceal the appearance of periorbital dyschromia but result in a non-naturally looking appearance. The opacity of a composition may be determined according to the Contrast Ratio method described in more detail below. The compositions herein have a contrast ratio of from 5 to 40 (e.g., 7 to 30, or 8 to 20).

Dermatologically Acceptable Carrier

The compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil or oil-in-water). The oil phase of the present invention may comprise silicone oils, non-silicone oils such as hydrocarbon oils, esters, ethers, and the like, and mixtures thereof. The aqueous phase typically comprises water and water-soluble ingredients (e.g., water-soluble moisturizing agents, conditioning agents, anti-microbials, humectants and/or other skin care actives).

Optional Ingredients

The present composition may optionally include one or more additional ingredients commonly used in cosmetic compositions (e.g., colorants, skin tone agents, skin anti-aging agents, anti-inflammatory agents, sunscreen agents, combinations of these and the like), provided that the additional ingredients do not undesirably alter the periorbital dyschromia appearance improvement benefit provided by the present composition. When present, the additional ingredients may be included at amounts of from 0.0001% to 50%; from 0.001% to 20%; or even from 0.01% to 10%, by weight of the composition. The additional ingredients, when incorporated into the composition, should be suitable for use in contact with human skin tissue without undue toxicity, incompatibility, instability, allergic response, and the like. Some nonlimiting examples of additional ingredients which may be suitable for use herein are described in U.S. Publication Nos. 2006/0275237 and 2004/0175347, both filed by Bissett, et al.

In some instances, the compositions used according to the present method include from 0.001% to 40% (e.g., from 1% to 30%, or from 2% to 20%) of one or more particulate materials and/or cosmetic powders to provide acute look and/or feel benefits. These particulates can, for instance, be platelet shaped, spherical, elongated or needle-shaped, or irregularly shaped; surface coated or uncoated (e.g., hydrophobically coated); porous or non-porous; charged or uncharged; and can be added to the current compositions as a powder or as a pre-dispersion. For example, pigmentary-grade metal oxide particles (e.g., having an average primary particle size greater than 100 nm or from 100 nm to 500 nm) may optionally be included to provide an appearance benefit. Some nonlimiting examples of particulate materials for use herein are described in U.S. Publications Nos. 2012/0021027, 2010/0074928, 2010/0003205, 2010/0003293 and 2013/0243835.

In another example, the compositions used in accordance with the present method may include powders in the form of spherical particles, provide an acute look and/or feel benefit. Spherical particle powders tend to improve the speed that the product appears to absorb into the skin, which helps provide increased control over product application (e.g., less likely to get into the eye and cause irritation). Spherical particle powders herein have a median particle size of 2 µm to 40 µm, (e.g., 3 µm to 25 µm or even 5 µm to 15 µm). Spherical particle powders can also increase the smooth feeling of the product film on the skin. Accordingly, it may be desirable to select spherical particles that have no tackiness and a rubber hardness (as measured by Durometer A defined in JIS K 6253) in the range of 10 to 90, (e.g., 20 to 80 or even from 25 to 75). In a particularly suitable example, the composition includes 2% to 20% (e.g., 4% to 12%) spherical silicone elastomer particles or spherical starch particles. The amount of silicone elastomer powder in the composition is determined based on the particulate material being in neat form (i.e., not swollen in solvent). Some nonlimiting examples of spherical particle powders are described in co-pending U.S. Ser. Nos. 14/596,360 and 14/596,374, filed by Jansen, et al., on Jan. 14, 2015.

Methods of Use

The compositions herein are intended for topical application to a target skin surface disposed in the periorbital region of a person who exhibits periorbital dyschromia. The target skin surface may be identified by the person exhibiting the periorbital dyschromia (e.g., via a self-assessment), an expert grader (e.g., in-person or from an image of the person), a diagnostic device in combination with a suitable diagnostic method (e.g., a digital camera in combination with suitable image analysis software) or a combination of these. The composition may be applied to the dyschromic portion of skin about once a day, twice a day, or even more frequently during a treatment period. In some instances the composition may be applied one or more times per week but less than once per day, e.g., 2, 3, 4, 5, or 6 time per week. It may be desirable to apply the composition locally. As used herein, "localized", "local", and "locally" mean that the composition is delivered to the targeted area of skin (i.e., the target portion of periorbital skin exhibiting periorbital dyschromia) while minimizing delivery to portions of skin not requiring treatment. For example, the composition may be applied to the target skin surface in Zones 1, 2 and/or 3, depending on the type of periorbital dyschromia being treated, and lightly massaged into the target skin surface. Alternatively, the composition may be applied to the entire periorbital region or even the entire face. Alternatively, general application refers to applying the composition to the target area of skin and one or more areas of skin other than the target area. For example, a skin care composition that is applied to the entire face including a target portion of skin in the periorbital region is applied generally. When used as intended, the present compositions improve the appearance of periorbital dyschromia, especially Type II and/or Type III periorbital dyschromia, as evidenced by a positive score on the Visual Perception Scale ("VPS"); a decrease in blood perfusion; an increase in L* value; a decrease in a* value; and/or an increase in b* value.

The form of the composition or the dermatologically acceptable carrier should be selected to facilitate application. In some instances, the composition may be delivered with an applicator suitable for general and/or localized application. For example, the applicator may be configured to suitably apply from 1 to 50 µL/cm$^2$ of composition (e.g., between 1 and 5 µL/cm$^2$) to a target skin surface. Of course, it will be appreciated that applicators are not required and the personal care composition herein can also be applied directly by using one's finger or in other conventional manners.

Test Methods

Visual Perception Method

This method provides a way to quantitatively evaluate the change in appearance of periorbital dyschromia using a Visual Perception Scale ("VPS"). The visual grading described herein is conducted by trained graders on captured images of the test subjects, but the method may also be readily adapted for use by consumers in self-diagnosing periorbital dyschromia and/or by in vivo examination of the periorbital region of a person by another. For example, it may be desirable to train beauty consultants who interact with consumers in a retail environment to classify periorbital dyschromia. Comparisons of baseline images collected at week 0 versus subsequent time point images are performed. The degree of change is scored using a −4 to +4 Magnitude Scale as shown below in Table 1. Negative numbers indicate that the periorbital dyschromia appeared better at baseline, while positive numbers reflect an improvement of the subject's appearance relative to baseline. The area of the periorbital region graded encompasses the area of the eye socket generally under the eye, extending from the inner corner of the eye, along the cheek bone and around to the outer corner of the eye, inclusive of the lateral orbital rim. The area of the periorbital region graded in this method does not include the area directly below the lower eyelid (as demarcated by the lower eyelashes), the upper eyelid or the upper eye socket. Features considered by the graders include: 1) the relative appearance of the darkness of the discoloration of the periorbital dyschromia compared to the surrounding skin tone; 2) the amount of affected area, footprint or pattern of the periorbital dyschromia; and 3) the appearance of the pigmentation hues involved in the discoloration and their intensity.

TABLE 1

Magnitude Scale

| Grade | Anchor | Description |
|---|---|---|
| +4 | Outstandingly Improved | Significant improvement in contrast, area and/or intensity throughout the graded area; outstanding improvement is immediately seen. |
| +3 | Obviously Improved | Readily seen improvements in contrast, area and/or intensity are obvious almost instantly. |
| +2 | Visibly Improved | Visible improvement in contrast, area and/or intensity is able to be seen within a few seconds. |
| +1 | Perceptibly Improved | Improvement in contrast, area and/or intensity are perceived after careful study. |
| 0 | Neutral/No Difference | No changes, or equivalent positive and negative changes, in the graded area.*<br>* Images should not be over scrutinized; images requiring more than 30 seconds of study to identify a change should be scored as having "zero" change. |
| −1 | Perceptibly Worsened | Worsening in contrast, area and/or intensity are perceived after careful study. |
| −2 | Visibly Worsened | Visible worsening in contrast, area and/or intensity is able to be seen within a few seconds. |
| −3 | Obviously Worsened | Readily seen worsening in contrast, area and/or intensity are obvious almost instantly. |
| −4 | Outstandingly Worsened | Significant worsening in contrast, area and/or intensity throughout the graded area; outstanding improvement is immediately seen. |

Blood Perfusion Method

Blood perfusion is generally recognized as the process of delivering blood to a capillary bed in biological tissue. Blood vessels and blood in the capillary beds of the periorbital region may be visible through the relatively thin periorbital skin. Thus, when less blood is visible in and around the capillary beds of the periorbital skin, there is a corresponding improvement in the appearance of periorbital dyschromia. The Blood Perfusion Method provides a suitable method of measuring the change in the amount of blood present in the capillary beds of periorbital skin.

The Blood Perfusion Method uses a blood perfusion imager (e.g., PeriCam™ PSI brand imager or equivalent), which is based on Laser Speckle Contrast Analysis ("LASCA") technology, in conjunction with PIMsoft™ brand dedicated application software or equivalent to visualize tissue blood perfusion in real-time. Test subjects are comfortably seated within 10 to 25 cm of the imager and instructed to close their eyes. Three images (i.e., perfusion, intensity and a standard color image) of the test subject's face are captured and recorded by the imager in accordance with the manufacturer's instructions. Using the dedicated application software, the periorbital regions of the test subject are masked (i.e., designated as regions of interest) to obtain the perfusion measurement in a periorbital region of interest. Masking is described in more detail below in the Imaging Method.

Contrast Ratio Method

Herein, "contrast ratio" refers to the opacity of a composition (i.e., the ability of the composition to reduce or prevent light transmission), determined after the composition is drawn onto an opacity chart (Form N2A, Leneta Company of Manwah, N.J. or the equivalent thereof). Contrast Ratio is measured using a spectrophotometer with settings selected to exclude specular reflection. The composition is applied to the top of the opacity chart and then is drawn into a film having a thickness of approximately 25 microns using a film applicator (e.g., as commercially available from BYK Gardner of Columbia, Md., or the equivalent thereof). The film is allowed to dry for 2 hours under conditions of 22° C.+/−1° C., 1 atm. Using a spectrophotometer with the settings selected to exclude specular reflection, the Y tristimulus value (i.e., the XYZ color space of the film) of the product film is measured and recorded. The Y tristimulus value is measured in three different areas of the product film over the black section of the opacity chart, and also in three different areas of the product film over the white section of the opacity chart.

The contrast ratio is calculated as the mathematical average of the three Y tristimulus values over the black areas, divided by the mathematical average of the three Y tristimulus values over the white areas, times 100:

$$\text{Contrast Ratio} = \frac{\text{average }(Y\text{black})}{\text{average }(Y\text{white})} \times 100$$

Imaging Method

This method provides a means for capturing a reproducible and analyzable image for determining L*a*b* values and for VPS testing. Any suitable image capture device along with imaging software and other associated ancillary equipment (e.g., computer and lights) may be used. A particularly suitable imaging system is the Visia-CR® brand imaging system, available from Canfield Scientific, New Jersey. The Visia® brand imaging system incorporates a Canon® brand EOS-1Ds Mk III SLR camera, which includes a CMOS sensor and provides 21.1 Mega pixel resolution (14-bit A/D converter).

Images may be collected under different lighting modalities using standard light, UV, cross-polarization, parallel-polarization or a combination of these. For example, the values and ranges described herein are reported using a (D65/2) light source. One skilled in the art will appreciate that these values can be reported at a wide range of different illuminations (D50, D75, Illuminant A, F2, F7, F11, TL84, etc. or 2 or 10 degree observer) according to well-known conversion methods, and when such conversions occur, the color values will typically change accordingly. In other words, even though the actual limits and/or ranges may change based on the conditions under which the image is captured, similar relationships among the values and ranges will still be seen. For example, if the camera has lower spectral sensitivity in the red channel than the camera described herein, the R channel response may be lower and the corresponding L*a*b* color values will be different, which in this case may result in lower a* values and/or higher b* values. Accordingly, different camera sensitivities, lightings and relevant exposures are contemplated, and the actual limits and/or ranges disclosed herein may vary according to the particular circumstances in which the image is captured without departing from the scope of the systems and/or methods described herein.

In preparation for image capture, test subjects are required to wash their faces and wait for at least 15 minutes to let their face dry. The hair of the subject is covered with a hairnet and the head and shoulders of the subject are covered with a black cloth. All jewelry that can be seen in an image area of interest is removed. The subject is positioned such that the subject's chin is resting comfortably on the chin rest of the imaging system, and a front image of the face (as opposed to a left-side or right-side image) can be suitably captured by the image capture device. After the subject is positioned, one or more images are captured (e.g., between 1 and 24, 2 and 20 or even between 3 and 15) with the subject's eyes open. It can be important to ensure that the subject's eyes are open when the image is captured, otherwise the closed upper eyelid may cause an inaccurate pigmentation reading. The captured image(s) are processed by converting the raw image to a .jpg file format.

Next, the .jpg format image is analyzed by a computer with suitable image analysis software. In some instances, it may be desirable to analyze only a portion of the image (e.g., Zone 1, 2 and/or 3 of the periorbital region). The portion of the image to be analyzed may be "masked" using image editing software such as Photoshop® or ImageJ® brand software. The masked region can then be isolated and analyzed as a separate image. It is to be appreciated that the image need not necessarily be masked for suitable analysis, and in some instances the entire image may be analyzed. In some instances, it may be desirable to reduce the size of the image, mask and/or region of interest by several pixels (e.g., between 5 and 15 pixels) around the outer edge of the image where some shadowing may occur.

The RGB values in the image, which are device dependent are converted to L*a*b* values. The L*a*b* values can be calculated using a suitable RGB conversion tool at D65 Illuminant and 2 degree observer (i.e., D65/2) (e.g., software installed on the computer or a suitable conversion tool found online). The conversion from RGB values to L*a*b* values can be performed on the entire image, a portion thereof or on one or more individual pixels. The resulting L*a*b* values may be averaged to provide average values for the image, mask or region of interest.

In some instances, the pixels may be analyzed individually and each pixel classified as corresponding to a particular type of periorbital dyschromia based on one or more of the L*a*b* values. When analyzed individually, the pixels may be analyzed according to their distribution across the different types of periorbital dyschromia. Since color may be perceived as being relative, depending on, for example, which instruments and/or imaging system is used, it can be important to color correct the masked region for each subject using a suitable color correction technique (e.g., according to International Color Consortium standards and practices), which helps make the color determination by the system less instrument specific. In some instances, it may be desirable to normalize the color in a region of interest (e.g., a masked region) to the basal skin tone of a nearby region (e.g., cheek). For example, the basal skin tone of the cheek may be obtained by masking a region of interest in the cheek (e.g., as illustrated in FIG. 8 or 9) and converting the RGB values in the masked region to L*a*b* values as described above. The resulting basal skin tone values for the cheek may then be subtracted from the corresponding values in the region of interest to provide normalized values. Color normalization may be performed on the entire region of interest (e.g., an average value for the ROI) or on a pixel by pixel basis for some or all of the pixels in the ROI, which may be 200,000 or more pixels.

EXAMPLES

Example 1—Formulation Examples

Table 2 shows five exemplary oil-in-water emulsion cosmetic compositions for use according to the present method. Compositions A to E may be prepared as follows. Combine the water phase ingredients in a suitable vessel and heat to 75° C. In a separate suitable vessel, combine the oil phase ingredients and heat to 75° C. Add the oil phase to the water phase and mill the resulting emulsion (e.g., with a TEKMAR™ T-25 or equivalent). Add the thickener to the emulsion and cool to 45° C. while stirring. At 45° C., add the remaining ingredients. Cool the product with stirring to 30° C. and pour into suitable containers.

TABLE 2

|  | A | B | C | D | E |
|---|---|---|---|---|---|
| Water Phase: | | | | | |
| Water | qs | qs | qs | qs | qs |
| Glycerin | 3.0 | 5.0 | 7.0 | 10.0 | 15.0 |
| Disodium EDTA | 0.1 | 0.1 | 0.05 | 0.1 | 0.1 |
| Methylparaben | 0.1 | 0.1 | 0.1 | 0.1 | 0.1 |
| Niacinamide | 2.0 | 0.5 | 3.5 | 3.0 | 5.0 |
| D-panthenol | 0.5 | 0.1 | 1.0 | 0.5 | 1.5 |
| Sodium Hydroxide | 0.001 | 0.002 | 0.001 | 0.001 | 0.001 |
| Benzyl alcohol | 0.25 | 0.25 | 0.25 | 0.25 | 0.25 |
| FD&C Red #40 | — | — | — | 0.0005 | — |
| Vicia faba extract[4] | 1.0 | — | — | 1.0 | 2.0 |
| Cucurbita pepo extract[5] | — | 1.0 | 1.0 | 1.0 | 0.1 |
| ADIPOLESS[6] | 2% | — | — | 1% | 0.1% |
| UNISOOTH[7] | — | 3% | — | 1.5% | 0.1% |
| HALOXYL[8] | — | — | 3% | — | 3% |
| Palmitoyl-pentapeptide[1] | 0.0002 | — | — | — | 0.0003 |
| N-acetyl glucosamine | 2.0 | — | 2.0 | — | 5.0 |
| Oil Phase: | | | | | |
| Isohexadecane | 3.0 | 3.0 | 3.0 | 4.0 | 3.0 |
| Isopropyl Isostearate | 1.0 | 0.5 | 1.3 | 1.5 | 1.3 |
| Sucrose polyester | 0.7 | — | 0.7 | 1.0 | 0.7 |
| Octinoxate | — | — | — | — | 6.0 |
| Avobenzone | — | — | — | 2.0 | 0.5 |
| Ethylhexyl methoxycrylene | — | — | — | — | 0.5 |
| Homosalate | — | — | — | 4.0 | — |
| Octisalate | — | — | — | 4.0 | — |
| Octocrylene | — | — | — | 2.0 | — |

TABLE 2-continued

|  | A | B | C | D | E |
|---|---|---|---|---|---|
| Phytosterol | — | — | — | 0.1 | — |
| Cetyl alcohol | 0.4 | 0.3 | 1.0 | 0.5 | 0.4 |
| Stearyl alcohol | 0.5 | 0.35 | 1.0 | 0.6 | 0.5 |
| Behenyl alcohol | 0.4 | 0.3 | 1.0 | 0.5 | 0.4 |
| PEG-100 stearate | 0.1 | 0.1 | 0.1 | 0.2 | 0.1 |
| Stearic Acid | 0.1 | 0.05 | 0.1 | 0.2 | 0.1 |
| Cetearyl glucoside | 0.1 | 0.1 | 0.1 | 0.25 | 0.1 |
| Thickener: | | | | | |
| Polyacrylamide/C13-14 isoparaffin/laureth-7 | 1.5 | — | 2.0 | 2.5 | 2.0 |
| Sodium acrylate/sodium acryloyldimethyl taurate copolymer/isohexadecane/polysorbate 80 | — | 3.0 | — | — | — |
| Additional Ingredients: | | | | | |
| KTZ Interfine ™ Gold[2] | 2.5 | — | 0.3 | — | 0.5 |
| KTZ Interfine ™ Red[2] | — | 1.0 | — | — | 0.5 |
| Tapioca Starch | — | 5.0 | — | 2.0 | 0.5 |
| Dry Flo TS[3] | 8.0 | — | 1.5 | — | — |
| Dimethicone/dimethiconol | — | 1.0 | 2.0 | 0.5 | 2.0 |
| Fragrance | — | 0.1 | 0.1 | 0.1 | 0.1 |
| Polymethylsilsequioxane | — | — | 0.25 | — | 1.0 |
| Nylon-12 | — | 0.5 | — | — | — |
| Total: | 100% | 100% | 100% | 100% | 100% |

[1]Palmitoyl-lysine-threonine-threonine-lysine-serine available from Sederma (France)
[2]Titanium dioxide coated mica available from Kobo Products Inc.
[3]Tapioca starch and polymethylsilsesquioxane from Akzo Nobel
[4]FOLLISYNC from Ashland Specialty Ingredients, New Jersey
[5]OCALINE PF from Soliance, France
[6]From Seppic, France.
[7]From Induchem, New York
[8]From Sederma, France.

Table 3 shows five exemplary silicone-in-water emulsion cosmetic compositions for use according to the present method. Compositions F to J may be prepared as follows. In a suitable vessel, combine the water phase ingredients and mix until uniform. In a separate suitable container, combine the silicone/oil phase ingredients and mix until uniform. Add half the thickener and then the silicone/oil phase to the water phase and mill the resulting emulsion (e.g., with a Tekmar™ T-25). Add the remainder of the thickener and then the remaining ingredients to the emulsion while stirring. Once the composition is uniform, pour the product into suitable containers.

TABLE 3

|  | F | G | H | I | J |
|---|---|---|---|---|---|
| Water Phase: | | | | | |
| Water | qs | qs | qs | qs | qs |
| Glycerin | 3.0 | 5.0 | 7.0 | 10.0 | 15.0 |
| Disodium EDTA | 0.1 | 0.1 | 0.05 | 0.1 | 0.1 |
| Niacinamide | 2.0 | 0.5 | 3.5 | 3.0 | 5.0 |
| D-panthenol | 0.5 | 0.1 | 1.0 | 0.5 | 1.5 |
| *Cucurbita pepo* extract[9] | 1.0 | — | 0.1 | 10.5 | 1.5 |
| *Vicia faba* extract[10] | — | 1.0 | 2.0 | 0.1 | — |
| FD&C Yellow #10 | — | — | — | — | 0.0004 |
| Palmitoyl-pentapeptide[1] | 0.0002 | — | — | — | 0.0003 |
| N-acetyl glucosamine | 2.0 | — | 2.0 | — | 5.0 |
| ADIPOLESS[11] | 1.0 | — | — | 2.0 | 1.0 |
| UNISOOTH[12] | — | 3.0 | — | — | 1.0 |
| HALOXYL[13] | 2.0 | — | 3.0 | — | 1.0 |
| Silicone/Oil Phase: | | | | | |
| Cyclomethicone D5 | 10.0 | 5.0 | 5.0 | 10.0 | 7.5 |
| Dow Corning ® 9040 silicone elastomer[2] | — | 10.0 | 5.0 | 5.0 | 7.5 |
| KSG-15AP silicone Elastomer[3] | 5.0 | — | 5.0 | 5.0 | 7.5 |
| Dimethione/dimethiconol | — | 2.0 | 2.0 | 1.0 | 2.0 |
| Dimethicone 50 csk | 1.0 | — | — | — | — |
| Laureth-4 | 0.2 | 0.2 | 0.3 | 0.2 | 0.2 |
| Vitamin E Acetate | — | 0.5 | — | 0.1 | — |
| Thickener: | | | | | |
| Polyacrylamide/C13-14 isoparaffin/laureth-7 | 2.5 | 2.5 | 3.0 | — | — |
| Sodium acrylate/sodium acryloyldimethyl taurate copolymer/isohexadecane/polysorbate 80 | — | — | — | 3.0 | — |
| Acrylates/C10-30 alkyl acrylates crosspolymer | — | — | — | — | 0.5 |
| Additional Ingredients: | | | | | |
| KSP 100[4] | 6.0 | 1.5 | — | — | — |
| KTZ Interval ™ Green[5] | — | 0.35 | — | 1.0 | 0.8 |
| Prestige Silk ™ Blue[6] | — | — | 1.5 | — | — |

TABLE 3-continued

|  | F | G | H | I | J |
|---|---|---|---|---|---|
| Cosmica ™ Orange[7] | — | — | — | 0.1 | — |
| Dry Flo TS[8] | — | 1.5 | 8.0 | — | — |
| Fragrance | — | 0.1 | 0.1 | 0.1 | 0.1 |
| Triethanolamine | — | — | — | — | 0.6 |
| PTFE | — | 0.5 | — | — | — |
| Polymethylsilsequioxane | — | 0.5 | 1.0 | — | — |
| Polyethylene | — | 0.5 | — | — | 1.0 |
| Total: | 100% | 100% | 100% | 100% | 100% |

[1]Palmitoyl-lysine-threonine-threonine-lysine-serine available from Sederma (France)
[2]A silicone elastomer dispersion from Dow Corning Corp.
[3]A silicone elastomer dispersion from Shin Etsu
[4]Vinyl dimethicone/methicone silsesquioxane crosspolymer from Shinetsu
[5]Titanium dioxide coated mica from Kobo Products Inc.
[6]Titanium dioxide and tin oxide coated mica from Eckart.
[7]Iron oxide coated mica from Engelhard Corporation.
[8]Tapioca starch and polymethylsilsesquioxane from Akzo Nobel
[9]OCALINE PF from Soliance, France
[10]FOLLISYNC from Ashland Specialty Chemical, New Jersey
[11]From Seppic, France.
[12]From Induchem, New York
[13]From Sederma, France.

Table 4 shows two exemplary water-in-silicone emulsion cosmetic compositions for use according to the present method. Compositions K and L may be prepared as follows. In a suitable vessel, blend the Phase A components with a suitable mixer until all of the components are dissolved. Blend Phase B components in suitable vessel and mix until uniform. Add Phase A slowly to Phase B with mixing and continue mixing until uniform. Mill the resulting product for about 5 minutes using an appropriate mill (e.g., TEKMAR T-25). Next, add Phase C while stirring the product. Continue mixing until the product is uniform, and pour the product into suitable containers.

TABLE 4

|  | K | L |
|---|---|---|
| Phase A |  |  |
| Water | q.s. | q.s. |
| Allantoin | 0.2 | 0.2 |
| Disodium EDTA | 0.1 | 0.1 |
| Ethyl paraben | 0.2 | 0.2 |
| Propyl paraben | 0.1 | 0.1 |
| BHT | 0.015 | 0.015 |
| D-panthenol | 1.0 | 0.5 |
| Glycerin | 7.5 | 13.0 |
| Niacinamide | 2.0 | 3.5 |
| Palmitoyl-pentapeptide[1] | — | 0.0003 |
| Benzyl alcohol | 0.2500 | 0.2500 |
| Green tea extract | 1.0 | 0.1 |
| Cucurbita pepo extract[6] | — | 2.2 |
| Vicia faba extract[7] | 1.0 | — |
| ADIPOLESS[8] | 2.0 | — |
| UNISOOTH[9] | — | 3.0 |
| Sodium metabisulfite | 0.1 | 0.01 |
| Phase B |  |  |
| Cyclopentasiloxane | 15.0000 | 15.0000 |
| C12-C15 alkyl benzoate | 1.5 | — |
| Vitamin E acetate | 0.5 | 0.1 |
| Retinyl propionate | 0.15 | — |
| Phytosterol | 0.1 | — |
| KSG-21 silicone elastomer[2] | 4.0 | 4.0 |
| Dow Corning ® 9040 silicone elastomer[3] | 15.0 | 15.0 |
| Abil ™ EM-97 dimethicone copolyol[4] | 0.5 | — |
| Polymethylsilsesquioxane | 2.5 | 0.5 |
| Fragrance | — | 0.1 |

TABLE 4-continued

|  | K | L |
|---|---|---|
| Phase C |  |  |
| KTZ Interval ™ Red-11S2[5] | — | 0.3 |

[1]Palmitoyl-lysine-threonine-threonine-lysine-serine available from Sederma (France)
[2]KSG-21 is an emulsifying silicone elastomer available from Shin Etsu
[3]A silicone elastomer dispersion from Dow Corning Corp
[4]Abil EM-97 available from Goldschmidt Chemical Corporation
[5]Silane surface treated titanium dioxide coated mica from Kobo Products Inc.
[6]OCALINE PF from Soliance, France.
[7]FOLLISYNC from Ashland Specialty Ingredients, New Jersey
[8]From Seppic, France.
[9]From Induchem, New York
[10]From Sederma, France.

Table 5 shows examples of personal care compositions for use in the present method. The compositions may be prepared by first combining the water phase ingredients in a container and mixing while heating to ~75° C. until uniform. Meanwhile, the ingredients of part 1 of the oil phase are weighed into a separate container and mixed while heating to ~75° C. until uniform. Once both respective phases are uniform, part 1 of the oil phase is added to the water phase. The resulting mixture is subjected to high shear mixing (e.g., Flacktek Speedmixer, or rotor-stator mill) and then cooled while stirring. When the temperature, reaches ~60° C., the thickener is then added while continuing to stir. Finally, when the batch reaches ~50° C., the Oil Phase Part 2 is added ingredients are added individually as cooling continues. At ~40° C., the active (i.e., pumpkin seed extract) is added while stirring. Once all ingredients are in the formulation and the temperature is ~40° C., the resulting mixture is again subjected to high shear mixing, and then the product is poured into suitable containers.

TABLE 5

|  | M | N | O | P | Q | R |
|---|---|---|---|---|---|---|
| Water Phase: |  |  |  |  |  |  |
| Water | 84.26 | 84.22 | 84.17 | 84.02 | 83.77 | 83.27 |
| Glycerin | 5.0 | 5.0 | 5.0 | 5.0 | 5.0 | 5.0 |
| Disodium EDTA | 0.1 | 0.1 | 0.1 | 0.1 | 0.1 | 0.1 |
| Oil Phase Part 1: |  |  |  |  |  |  |
| Isohexadecane | 3.0 | 3.0 | 3.0 | 3.0 | 3.0 | 3.0 |
| Isopropyl Isostearate | 1.33 | 1.33 | 1.33 | 1.33 | 1.33 | 1.33 |
| Polymethyl-silsesquioxane | 0.25 | 0.25 | 0.25 | 0.25 | 0.25 | 0.25 |
| Cetearyl Glucoside, Cetearyl Alcohol | 0.20 | 0.20 | 0.20 | 0.20 | 0.20 | 0.20 |
| Behenyl Alcohol | 0.40 | 0.40 | 0.40 | 0.40 | 0.40 | 0.40 |
| Ethylparaben | 0.20 | 0.20 | 0.20 | 0.20 | 0.20 | 0.20 |
| Propylparaben | 0.10 | 0.10 | 0.10 | 0.10 | 0.10 | 0.10 |
| Cetyl Alcohol | 0.32 | 0.32 | 0.32 | 0.32 | 0.32 | 0.32 |
| Stearyl Alcohol | 0.48 | 0.48 | 0.48 | 0.48 | 0.48 | 0.48 |
| PEG-100 Stearate | 0.10 | 0.10 | 0.10 | 0.10 | 0.10 | 0.10 |
| Thickener: |  |  |  |  |  |  |
| Sepigel 305[1] | 2.00 | 2.00 | 2.00 | 2.00 | 2.00 | 2.00 |
| Oil Phase Part 2: |  |  |  |  |  |  |
| Benzyl Alcohol | 0.25 | 0.25 | 0.25 | 0.25 | 0.25 | 0.25 |
| DC 1503[2] | 2.00 | 2.00 | 2.00 | 2.00 | 2.00 | 2.00 |
| Active: |  |  |  |  |  |  |
| Cucurbita pepo extract[3] | .01% | 12% | — | — | 2% | 5% |
| Vicia faba extract[4] | 1.0% | — | 2.0% | 6% | — | 1% |
| ADIPOLESS[5] | 2.0% | — | 1.0% | 0.5% | — | — |

TABLE 5-continued

|  | M | N | O | P | Q | R |
|---|---|---|---|---|---|---|
| UNISOOTH[6] | — | 3.0% | — | 2.0% | 3.0% | |
| HALOXYL[7] | — | — | 3.0% | 0.5% | | 3.0% |
| Total: | 100% | 100% | 100% | 100% | 100% | 100% |

[1]Polyacrylamide, C13-14 isoparaffin, and laureth-7, from Seppic, France.
[2]Dimethicone and Dimethiconol from Dow Corning, Inc., Midland, MI.
[3]OCALINE PF from Soliance, France.
[4]FOLLISYNC from Ashland Specialty Ingredients, New Jersey
[5]From Seppic, France.
[6]From Induchem, New York
[7]From Sederma, France.

Example 2: In Vivo Study (VPS, Blood Perfusion and Imaging)

This example demonstrates the ability of the present method to improve the appearance of Type II and Type III periorbital dyschromia. Twenty-five Caucasian female test subjects aged 20 to 60 were enrolled in a nine-week, split-face, round-robin design study to evaluate the ability of various chronic actives to improve the appearance of Type I, Type II, and/or Type III periorbital dyschromia. The oil-in-water emulsion of Example R from Table 5 was evaluated in this study, except that the amount of chronic active (Type I or Type II) was changed, as indicated below.

During the study, the under eye portion of the periorbital region (i.e., the shaded area 400 in FIG. 4A) on the left side of the test subject's face was treated with the test composition, and the under eye portion of the periorbital region on the right side of the test subject's face was treated with a vehicle control (i.e., the same composition as the test composition except without the chronic active). The amount of chronic active included in each test composition is shown in the Tables below. The test subjects were instructed to use cleansing cloths and a facial moisturizer, which were provided to them, twice a day. The test subjects were also instructed to refrain from using any eye treatment products during the course of the study and to avoid excessive UV exposure that could result in facial sunburn or tanning. The test subjects were permitted to use their normal makeup products (e.g., foundation, blush, eye and lip liners) five minutes after application of the under eye compositions, but were asked not to switch brands. The test subjects applied the control and test compositions twice a day; once in the morning and once in the evening at least 30 minutes before going to bed. Approximately 0.04 g or 40-50 µl of each composition was applied to the periorbital skin under the appropriate eye. Images of the test subjects and blood perfusion data were collected at weeks 0 (baseline), 2, 4 and 8 for use in the Visual Perception Scale, Imaging and Blood Perfusion Methods described above. The baseline values were determined at the start of the test (week 0). The control values shown in the Tables below are an average across all test subjects.

The results of the in vivo study using Type II actives (i.e., 1% fava bean extract and 5% pumpkin seed extract) are illustrated below in Tables 6 to 8 for test subjects exhibiting Type II periorbital dyschromia and in Tables 9 to 11 for test subjects exhibiting Type III periorbital dyschromia. The results of the in vivo study using Type I actives (i.e., 3% UNISOOTH and 2% ADIPOLESS) are illustrated below in Tables 12 to 13 for test subjects exhibiting Type I periorbital dyschromia. The results shown in the Tables are averages of mean values. For each paired comparison, each endpoint was analyzed using a mixed model, which included subject (random effect), treatment effect, and fixed effects (side of the face and baseline). In this test, a one-sided p-value was used to compare the efficacy of the treatment as compared to control. P-values of 0.2 or less and 0.8 or more are considered statistically significant, and p-values of less than 0.3 but greater than 0.2 and less than 0.8 but greater than 0.7 are considered statistically trending. From the results, it can be seen that the selected chronic actives can provide an improvement in the appearance of periorbital dyschromia.

Table 6A shows the change in VPS relative to the baseline value for treatment of Type II periorbital dyschromia with an extract of *Vicia faba* versus a vehicle control. Table 6B shows the change in VPS relative to the baseline value for treatment of Type II periorbital dyschromia with an extract of *Cucurbita pepo* versus a vehicle control.

TABLE 6A

Type II - VPS (1% *Vicia faba* extract)

|  | Control | Test Composition | p-Value |
|---|---|---|---|
| Week 2 | −0.11 | 0.03 | 0.39 |
| Week 4 | 0.39 | 0.46 | 0.43 |
| Week 8 | −0.31 | 0.76 | 0.09 |

TABLE 6B

Type II - VPS (5% *Cucurbita pepo* extract)

|  | Control | Test Composition | p-Value |
|---|---|---|---|
| Week 2 | −0.11 | 0.79 | 0.04 |
| Week 4 | 0.39 | 1.03 | 0.08 |
| Week 8 | −0.31 | 0.66 | 0.10 |

Table 7A shows the change in blood perfusion value relative to the baseline value for treatment of Type II periorbital dyschromia with an extract of *Vicia faba* versus a vehicle control. Table 7B shows the change in blood perfusion value relative to the baseline value for treatment of Type II periorbital dyschromia with an extract of *Cucurbita pepo* versus a vehicle control.

TABLE 7A

Type II - Blood Perfusion (1% *Vicia faba* extract)

| Week | Control | Test Product | p-value |
|---|---|---|---|
| Week 2 | −9.48 | −19.9 | 0.27 |
| Week 4 | −5.5 | −25.4 | 0.15 |
| Week 8 | −11.2 | −22.2 | 0.17 |

TABLE 7B

Type II - Blood Perfusion (5% *Cucurbita pepo* extract)

| Week | Control | Test Product | p-value |
|---|---|---|---|
| Week 2 | −9.48 | −3.34 | 0.72 |
| Week 4 | −5.5 | −8.27 | 0.37 |
| Week 8 | −11.2 | −2.55 | 0.77 |

Tables 8A shows the change in imaging values (i.e., L* value, a* value and b* value) relative to the baseline value for treatment of Type II periorbital dyschromia with an extract of *Vicia faba* versus a vehicle control. Tables 8B shows the change in imaging values (i.e., L* value, a* value and b* value) relative to the baseline value for treatment of Type II periorbital dyschromia with an extract of *Cucurbita pepo* versus a vehicle control

TABLE 8A

Type II - Imaging Values (1% *Vicia faba* extract)

| Endpoint | Week | Control | Test Product | p-value |
|---|---|---|---|---|
| L* | Week 2 | 0.99 | 1.26 | 0.25 |
| L* | Week 4 | 1.58 | 1.58 | 0.50 |
| L* | Week 8 | 1.04 | 1.19 | 0.32 |
| a* | Week 2 | −0.27 | −0.38 | 0.31 |
| a* | Week 4 | −0.45 | −0.6 | 0.19 |
| a* | Week 8 | −0.37 | −0.48 | 0.26 |
| b* | Week 2 | 0.42 | 0.52 | 0.30 |
| b* | Week 4 | 0.48 | 0.49 | 0.48 |
| b* | Week 8 | 0.32 | 0.34 | 0.46 |

TABLE 8B

Type II - Imaging Values (5% *Cucurbita pepo* extract)

| Endpoint | Week | Control | Test Product | p-value |
|---|---|---|---|---|
| L* | Week 2 | 0.99 | 1.15 | 0.35 |
| L* | Week 4 | 1.58 | 1.35 | 0.78 |
| L* | Week 8 | 1.04 | 1.32 | 0.21 |
| a* | Week 2 | −0.27 | −0.28 | 0.49 |
| a* | Week 4 | −0.45 | −0.41 | 0.59 |
| a* | Week 8 | −0.37 | −0.26 | 0.72 |
| b* | Week 2 | 0.42 | 0.36 | 0.62 |
| b* | Week 4 | 0.48 | 0.38 | 0.69 |
| b* | Week 8 | 0.32 | 0.33 | 0.48 |

Table 9A shows the change in VPS score relative to the baseline value for treatment of Type III periorbital dyschromia with an extract of *Vicia faba* versus a vehicle control. Table 9B shows the change in VPS score relative to the baseline value for treatment of Type III periorbital dyschromia with an extract of *Cucurbita pepo* versus a vehicle control.

TABLE 9A

Type III - VPS (1% *Vicia faba* extract)

| Week | Control | Test Product | p-Value |
|---|---|---|---|
| 2 | 0.63 | 0.45 | 0.61 |
| 4 | −0.66 | 0.24 | 0.06 |
| 8 | 0.76 | 0.56 | 0.59 |

TABLE 9B

Type III - VPS (5% *Cucurbita pepo* extract)

| Week | Control | Test Product | p-Value |
|---|---|---|---|
| 2 | 0.63 | −0.29 | 0.94 |
| 4 | −0.66 | −0.18 | 0.19 |
| 8 | 0.76 | 0.14 | 0.79 |

Table 10A shows the change in blood perfusion value relative to the baseline value for treatment of Type III periorbital dyschromia with an extract of *Vicia faba* versus a vehicle control. Table 10B shows the change in blood perfusion value relative to the baseline value for treatment of Type III periorbital dyschromia with an extract of *Cucurbita pepo* versus a vehicle control.

TABLE 10A

Type III - Blood Perfusion (1% *Vicia faba* extract)

| Week | Control | Test Product | p-value |
|---|---|---|---|
| 2 | 2.59 | 4.78 | 0.53 |
| 4 | −16.8 | −24 | 0.31 |
| 8 | 10.91 | −22.1 | 0.03 |

TABLE 10B

Type III - Blood Perfusion (5% *Cucurbita pepo* extract)

| Week | Control | Test Product | p-value |
|---|---|---|---|
| 2 | 2.59 | 5.35 | 0.55 |
| 4 | −16.8 | −0.6 | 0.88 |
| 8 | 10.91 | −0.52 | 0.24 |

Table 11A shows the change in imaging values (i.e., L* value, a* value and b* value) relative to the baseline value for treatment of Type III periorbital dyschromia with an extract of *Vicia faba* versus a vehicle control. Table 11B shows the change in imaging values (i.e., L* value, a* value and b* value) relative to the baseline value for treatment of Type III periorbital dyschromia with an extract of *Cucurbita pepo* versus a vehicle control.

TABLE 11A

Type III - Imaging Values (1% *Vicia faba* extract)

| Endpoint | Week | Control | Test Product | p-value |
|---|---|---|---|---|
| L* | 2 | 1.1 | 0.62 | 0.83 |
| L* | 4 | 0.35 | 1.03 | 0.03 |
| L* | 8 | 1.3 | 1.12 | 0.65 |
| a* | 2 | 0.14 | 0.27 | 0.64 |
| a* | 4 | 0.37 | 0.14 | 0.14 |
| a* | 8 | −0.3 | −0.09 | 0.77 |
| b* | 2 | 0.27 | 0.01 | 0.75 |
| b* | 4 | 0.18 | 0.25 | 0.40 |
| b* | 8 | 0.48 | 0.43 | 0.55 |

TABLE 11B

Type III - Imaging Values (5% *Cucurbita pepo* extract)

| Endpoint | Week | Control | Test Product | p-value |
|---|---|---|---|---|
| L* | 2 | 1.1 | 0.62 | 0.83 |
| L* | 4 | 0.35 | 1.03 | 0.03 |
| L* | 8 | 1.3 | 1.12 | 0.65 |
| a* | 2 | 0.14 | 0.27 | 0.64 |
| a* | 4 | 0.37 | 0.14 | 0.14 |
| a* | 8 | −0.3 | −0.09 | 0.77 |
| b* | 2 | 0.27 | 0.01 | 0.75 |

TABLE 11B-continued

Type III - Imaging Values (5% Cucurbita pepo extract)

| Endpoint | Week | Control | Test Product | p-value |
|---|---|---|---|---|
| b* | 4 | 0.18 | 0.25 | 0.40 |
| b* | 8 | 0.48 | 0.43 | 0.55 |

Table 12A shows the change in VPS relative to the baseline value for treatment of Type I periorbital dyschromia with a mixture of Chenopodium quinoa seed extract and butylene glycol (ADIPOLESS from Seppic) versus a vehicle control. Table 12B shows the change in VPS relative to the baseline value for treatment of Type I periorbital dyschromia with a mixture of propyl gallate, gallyl glucoside, and epigallocatechin gallatyl glucoside (UNISOOTH from Induchem) versus a vehicle control.

TABLE 12A

Type I - VPS (2% ADIPOLESS)

| | Control | Test Composition | p-Value |
|---|---|---|---|
| Week 2 | −0.11 | 0.03 | 0.39 |
| Week 4 | 0.39 | 0.46 | 0.43 |
| Week 8 | −0.31 | 0.76 | 0.09 |

TABLE 12B

Type I - VPS (3% UNISOOTH)

| | Control | Test Composition | p-Value |
|---|---|---|---|
| Week 2 | −0.11 | 0.79 | 0.04 |
| Week 4 | 0.39 | 1.03 | 0.08 |
| Week 8 | −0.31 | 0.66 | 0.10 |

Table 13A shows the change in imaging values (i.e., L* value, a* value and b* value) relative to the baseline value for treatment of Type I periorbital dyschromia with a mixture of chenopodium quinoa seed extract and butylene glycol (ADIPOLESS from Seppic) versus a vehicle control. Table 13B shows the change in imaging values (i.e., L* value, a* value and b* value) relative to the baseline value for treatment of Type I periorbital dyschromia with a mixture of propyl gallate, gallyl glucoside, and epigallocatechin gallatyl glucoside (UNISOOTH from Induchem) versus a vehicle control.

TABLE 13A

Type I - Imaging Values (2% Adipoless)

| Endpoint | Week | Control | Test Product | p-value |
|---|---|---|---|---|
| L* | Week 2 | 0.06 | 0.39 | 0.09 |
| L* | Week 4 | 0.65 | 0.69 | 0.41 |
| L* | Week 8 | 0.60 | 0.77 | 0.20 |
| a* | Week 2 | −0.10 | −0.06 | 0.58 |
| a* | Week 4 | −0.20 | −0.21 | 0.47 |
| a* | Week 8 | −0.44 | −0.35 | 0.78 |
| b* | Week 2 | −0.08 | 0.03 | 0.27 |
| b* | Week 4 | 0.37 | 0.41 | 0.41 |
| b* | Week 8 | 0.19 | 0.22 | 0.43 |

TABLE 13B

Type I - Imaging Values (3% Unisooth)

| Endpoint | Week | Control | Test Product | p-value |
|---|---|---|---|---|
| L* | Week 2 | 0.06 | 0.47 | 0.05 |
| L* | Week 4 | 0.65 | 0.74 | 0.32 |
| L* | Week 8 | 0.60 | 0.55 | 0.59 |
| a* | Week 2 | −0.10 | −0.23 | 0.20 |
| a* | Week 4 | −0.20 | −0.41 | 0.1 |
| a* | Week 8 | −0.44 | −0.44 | 0.5 |
| b* | Week 2 | −0.08 | 0.13 | 0.12 |
| b* | Week 4 | 0.37 | 0.38 | 0.49 |
| b* | Week 8 | 0.19 | 0.20 | 0.48 |

Example 3: In Vitro Study (B16—Melanin Assay)

This example demonstrates the inability of pumpkin seed extract and fava bean extract to inhibit melanin synthesis. It is believed that an overabundance of melanin is a key contributor to the appearance of Type I periorbital dyschromia, but not for Type II periorbital dyschromia. Thus, treating Type I periorbital dyschromia with pumpkin seed extract or fava bean extract should not provide any improvement in its appearance, as demonstrated by the lack of melanin inhibition activity in a conventional B16 assay. This is important because it shows that it is important to select a chronic active that treats each type of periorbital dyschromia. For example, a composition that utilizes pumpkin seed extract may not improve the appearance of Type I periorbital dyschromia, and thus it may be desirable to also include a chronic active for treating Type I periorbital dyschromia in such a composition.

In this example, a commercially available B16-F1 mouse melanoma cell line from American Tissue Culture Collection, Virginia, USA was employed in a conventional melanin synthesis inhibition assay. The cell culture medium used in the assay is 500 mL of Dulbecco's Modified Eagle's Medium (DMEM), 50 mL Fetal Bovine Serum (FBS), and 5 mL of penicillin-streptomycin liquid. B16-F1 cells that are cultured in this medium and grown to greater than 90% confluency will synthesize melanin. While not intending to be bound by any theory, it is hypothesized that the melanin synthesis is stimulated by the culture medium and/or stress induced by growth to a high confluency. The DMEM and FBS can be obtained from American Tissue Culture Collection and the penicillin-streptomycin liquid can be obtained from Invitrogen, Inc., California, USA. Equipment used in the assay include a $CO_2$ incubator, such as a Forma Series Model 3110 by Therma Scientific, Massachusetts, USA; a hemocytometer, such as a Bright Line model by Hauser Scientific, Pennsylvania, USA; and a UV-Visible Spectrum Plate Reader, such as a SpectraMax250 from Molecular Devices, California, USA.

Day 0: To begin the assay, the cell culture medium is heated to 37° C. and 29 mL of the medium is placed into a T-150 flask. Approximately $1 \times 10^6$ of B16-F1 passage 1 mouse cells are added to the T-150 flask and incubated for 3 days at 37° C., 5% $CO_2$, 90% relative humidity, until ~80% confluency.

Day 3: The cells from the T-150 flask are trypsinized, and the concentration of cells is determined using the hemacytometer. Initiate a 96 well plate with 2,500 cells per well in 100 μL of cell culture medium. Incubate the plate at 37° C., 5% CO2, 90% relative humidity for 2 days until at least 20% to 40% confluent.

Day 5: Remove the cell culture medium from the plate and replace with fresh culture medium (100 uL per well). Add 1 uL of test compound diluted in a water solvent. Multiple dilution ratios may be tested in order to generate a dose response curve, wherein preferably three wells are treated with each dilution ratio. Positive and negative controls may include wells having the cell culture medium, B16-F1 cells, and the solvent (negative control), and wells comprising the cell culture medium, B16-F1 cells and a known melanin inhibitor (e.g., deoxyarbutin or kojic acid).

Day 7: Cells should have a confluency greater than ~90%. If not, this data point is not used. Add 100 uL of a 0.75% sodium hydroxide solution to each well. Read the 96 well plate using the UV-Vis Plate Reader at 410 nm to optically measure the amount of melanin produced between wells that are treated with the pumpkin seed extract and control wells that are not. Wells in which melanin is produced appear brownish in color. Wells in which little melanin is produced appear clear to light purple in color. Percentage of melanin synthesis inhibition is calculated by the following equation:

$$\frac{100 - [OD410 \text{ Test Compound} - OD410 \text{ Control \#2}] \times 100}{(OD410 \text{ Control \#1} - OD410 \text{ Control \#2})}$$

Where OD410 is the Optical Density at 410 nm as measured by the UV-Vis Spectrum Plate Reader.

When Control #3 is used, the formula for percentage melanin synthesis inhibition is:

$$\frac{100 - [OD410 \text{ Test Compound} - OD410 \text{ Control \#3}] \times 100}{(OD410 \text{ Control \#1} - OD410 \text{ Control \#2})}$$

The concentration of test agent needed to provide the IC 50 is recorded.

Table 12 shows the concentration of each composition needed to provide the IC 50. The positive controls used in this example are deoxyarbutin and kojic acid, both of which are well-known inhibitors of melanin synthesis. As shown in Table 12, the concentration of the test composition required to obtain IC 50 was much higher than either the deoxyarbutin or the kojic acid, suggesting that the pumpkin seed extract tested in this example is a poor inhibitor of melanin synthesis.

TABLE 14

B16 (IC 50)

| Composition | Concentration Needed for IC 50 (v/v) |
|---|---|
| Deoxyarbutin | 0.008 |
| Kojic Acid | 0.01 |
| Cucurbita pepo extract[1] | 0.4 |
| Vicia faba extract[2] | 2.0 |

[1]OCALINE PF from Soliance, France.
[2]FOLLISYNC from Ashland Specialty Ingredients, New Jersey Examples and Combinations A. A cosmetic composition for improving the appearance of periorbital dyschromia, comprising:
  i. an effective amount of a Type I active;
  ii. an effective amount of a Type II active;
  iii. a dermatologically acceptable carrier; and
  iv. a viscosity of from about 50,000 to about 200,000 centipoise.
B. The cosmetic composition of paragraph A, wherein the Type I active is a tocoquinone; panthenol; 5,5-dimethyl-1-pyrroline N-oxide; orotic acid; amino acetic acid; cyclohexane-1,2,3,4,5,6-hexol; 8-cyclopentyl-1,3-dipropylxanthine; lactobionic acid; a mixture of propyl gallate, gallyl glucoside, and epigallocatechin gallatyl glucoside; a salicylate; a vitamin B3 compound; undecylenoyl phenylalanine; a mixture of glycerin, steareth-20, n-hydroxysuccinimide, chrysin, palmitoyl tripeptide-1, and palmitoyl tetrapeptide-7; a mixture of Chenopodium quinoa seed extract and butylene glycol; or a combination of these.
C. The composition of paragraph A or B, wherein the Type II active is an extract of Vicia fava, an extract of Cucurbita pepo, cholecalciferol, or a combination of these.
D. The composition of any preceding paragraph, wherein the Type I and Type II actives are each present at about 0.0001% to about 15%.
E. The composition of any preceding paragraph, wherein the Type II active does not worsen the appearance of Type I periorbital dyschromia.
F. The composition of any preceding paragraph, wherein at least one of the Type I and Type II actives improve the appearance of Type III periorbital dyschromia.
G. The composition of any preceding paragraph, further comprising a Type III active.
H. The composition of paragraph G, wherein the Type III active is hydroxycinnamic acid, proline, or a combination of these.
I. The composition of any preceding paragraph, wherein the dermatologically acceptable carrier is an emulsion.
J. The composition of paragraph I, wherein the emulsion includes an oil phase comprising a silicone oil, a non-silicone oil, an ester, an ether, or a mixture of these.
K. The composition of paragraph I, wherein the emulsion includes an aqueous phase comprising water-soluble skin actives selected from moisturizing agents, conditioning agents, anti-microbials, skin tone agents, skin anti-aging agents, anti-inflammatory agents, and combinations of these.
L. A method of improving the appearance of periorbital dyschromia, comprising:
  i. identifying a target portion of skin exhibiting periorbital dyschromia; and
  ii. applying a personal care composition to the target portion of skin during a treatment period, wherein the personal care composition comprises an effective amount of a Type I active, an effective amount of a Type II active, a dermatologically acceptable carrier, and a viscosity of from about 50,000 to about 200,000 centipoise, and the treatment period is sufficient for the composition to improve the appearance of the periorbital dyschromia.
M. The method of paragraph L, wherein the Type I active includes a mixture of propyl gallate, gallyl glucoside, and epigallocatechin gallatyl glucoside, a mixture of Chenopodium quinoa seed extract and butylene glycol, or a combination of these.
N. The method of paragraph L or M, wherein the Type II active includes an extract of Vicia faba, an extract of Cucurbita pepo, cholecalciferol, or a combination of these.

O. The method of any preceding paragraph, wherein the Type I and Type II actives are each present at an amount of about 0.0001 wt % to about 5 wt %.
P. The method of any preceding paragraph, wherein the improvement in appearance of the periorbital dyschromia corresponds to a positive change in Visual Perception Scale score.
Q. The method of any preceding paragraph, wherein the improvement in appearance of the periorbital dyschromia corresponds to a decrease in blood perfusion.
R. The method of any preceding paragraph, wherein the improvement in appearance of the periorbital dyschromia corresponds to an increase in L* value, a decrease in a* value, an increase in b* value or a combination of these.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of improving the appearance of periorbital dyschromia, comprising:
 a. identifying a target portion of skin exhibiting periorbital dyschromia, wherein the target portion of skin is disposed in Zones 1 and 3 of a periorbital region of a user and includes brown, orange, and yellow tones; and
 b. applying a personal care composition to the target portion of skin during a treatment period, wherein the personal care composition comprises an effective amount of a Type I active, an effective amount of a Type II active, a dermatologically acceptable carrier, and a viscosity of about 50,000 to about 200,000 centipoise, and the treatment period is sufficient for the composition to improve the appearance of the periorbital dyschromia.

2. The method of claim 1, wherein the Type I active includes a mixture of propyl gallate, gallyl glucoside, and epigallocatechin gallatyl glucoside, a mixture of *Chenopodium quina* seed extract and butylene glycol, or a combination of these.

3. The method of claim 1, wherein the Type II active includes an extract of *Vicia faba*, an extract of *Cucurbita pepo*, cholecalciferol, or a combination of these.

4. The method of claim 1, wherein the Type I and Type II actives are each present at an amount of about 0.0001 wt % to about 5 wt %.

5. The method of claim 1, wherein the improvement in appearance of the periorbital dyschromia corresponds to a positive change in Visual Perception Scale score.

6. The method of claim 1, wherein the improvement in appearance of the periorbital dyschromia corresponds to a decrease in blood perfusion.

7. The method of claim 1, wherein the improvement in appearance of the periorbital dyschromia corresponds to an increase in L* value, a decrease in a* value, an increase in b* value or a combination of these.

* * * * *